United States Patent
Falahatpisheh et al.

(10) Patent No.: US 10,460,452 B2
(45) Date of Patent: *Oct. 29, 2019

(54) ULTRASOUND-BASED VOLUMETRIC PARTICLE TRACKING METHOD

(71) Applicant: The Regents of the University of California, Oakland, CA (US)

(72) Inventors: Ahmad Falahatpisheh, Irvine, CA (US); Arash Kheradvar, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/973,321

(22) Filed: May 7, 2018

(65) Prior Publication Data

US 2018/0253854 A1 Sep. 6, 2018

Related U.S. Application Data

(63) Continuation of application No. 14/941,294, filed on Nov. 13, 2015, now Pat. No. 9,962,142.
(Continued)

(51) Int. Cl.
*G06K 9/00* (2006.01)
*G06T 7/20* (2017.01)
(Continued)

(52) U.S. Cl.
CPC ............... *G06T 7/20* (2013.01); *A61B 8/06* (2013.01); *A61B 8/065* (2013.01); *A61B 8/463* (2013.01); *A61B 8/466* (2013.01); *A61B 8/483* (2013.01); *A61B 8/488* (2013.01); *A61B 8/5223* (2013.01); *G06K 9/4604* (2013.01); *G06K 9/4661* (2013.01); *G06T 7/0012* (2013.01);
(Continued)

(58) Field of Classification Search
CPC .................. G06T 2200/04; G06T 2207/30104
See application file for complete search history.

(56) References Cited

U.S. PATENT DOCUMENTS

2009/0238404 A1* 9/2009 Orderud ................. G16H 50/50
382/103
2010/0099991 A1* 4/2010 Snyder ................ G01S 15/8979
600/454
(Continued)

OTHER PUBLICATIONS

Barnhart, et al. 1994 "Phase-conjugate holographic system for high-resolution particle-image velocimetry" *Applied Optics* 33(30): 7159-7170.
(Continued)

*Primary Examiner* — Oneal R Mistry
(74) *Attorney, Agent, or Firm* — Knobbe, Martens, Olson & Bear LLP

(57) ABSTRACT

The disclosure relates to method of processing three-dimensional images or volumetric datasets to determine a configuration of a medium or a rate of a change of the medium, wherein the method includes tracking changes of a field related to the medium to obtain a deformation or velocity field in three dimensions. In some cases, the field is a brightness field inherent to the medium or its motion. In other embodiments, the brightness field is from a tracking agent that includes floating particles detectable in the medium during flow of the medium.

52 Claims, 24 Drawing Sheets

Related U.S. Application Data

(60) Provisional application No. 62/079,834, filed on Nov. 14, 2014, provisional application No. 62/113,929, filed on Feb. 9, 2015, provisional application No. 62/199,853, filed on Jul. 31, 2015.

(51) Int. Cl.

| | | |
|---|---|---|
| *G06T 7/00* | (2017.01) | |
| *G06K 9/46* | (2006.01) | |
| *A61B 8/06* | (2006.01) | |
| *A61B 8/00* | (2006.01) | |
| *A61B 8/08* | (2006.01) | |

(52) U.S. Cl.
CPC ...... *G06K 9/00577* (2013.01); *G06T 2200/04* (2013.01); *G06T 2207/10136* (2013.01); *G06T 2207/30104* (2013.01)

(56) References Cited

U.S. PATENT DOCUMENTS

| | | | |
|---|---|---|---|
| 2014/0071125 A1* | 3/2014 | Burlina | .......... G06T 17/00 345/420 |
| 2015/0094584 A1 | 4/2015 | Abe et al. | |
| 2015/0201908 A1 | 7/2015 | Kang et al. | |
| 2016/0018501 A1 | 1/2016 | Kimura | |

OTHER PUBLICATIONS

Elsinga, et al. 2006 "Tomographic particle image velocimetry" *Experiments in Fluids* 41(6): 933-947.

Falahatpisheh, et al. 2014 "Three-dimensional reconstruction of cardiac flows based on multi-planar velocity fields" *Experiments in fluids* 55(11): 1-15.

Kheradvar, et al. 2010 "Echocardiographic particle image velocimetry: A novel technique for quantification of left ventricular blood vorticity pattern" *Journal of the American Society of Echocardiography* 23(1): 86-94.

Pereira, et al. 2002 "Defocusing digital particle image velocimetry and the three-dimensional characterization of two-phase flows" *Meas Sci Technol*. 13: 683-694.

Stanislas, et al. "Main results of the third international PIV challenge" *Experiments in Fluids* 45(1): 27-71.

Westerweel, et al. 2013 "Particle image velocimetry for complex and turbulent flows" *Annual Review of Fluid Mechanics* 45(1): 409-436.

\* cited by examiner

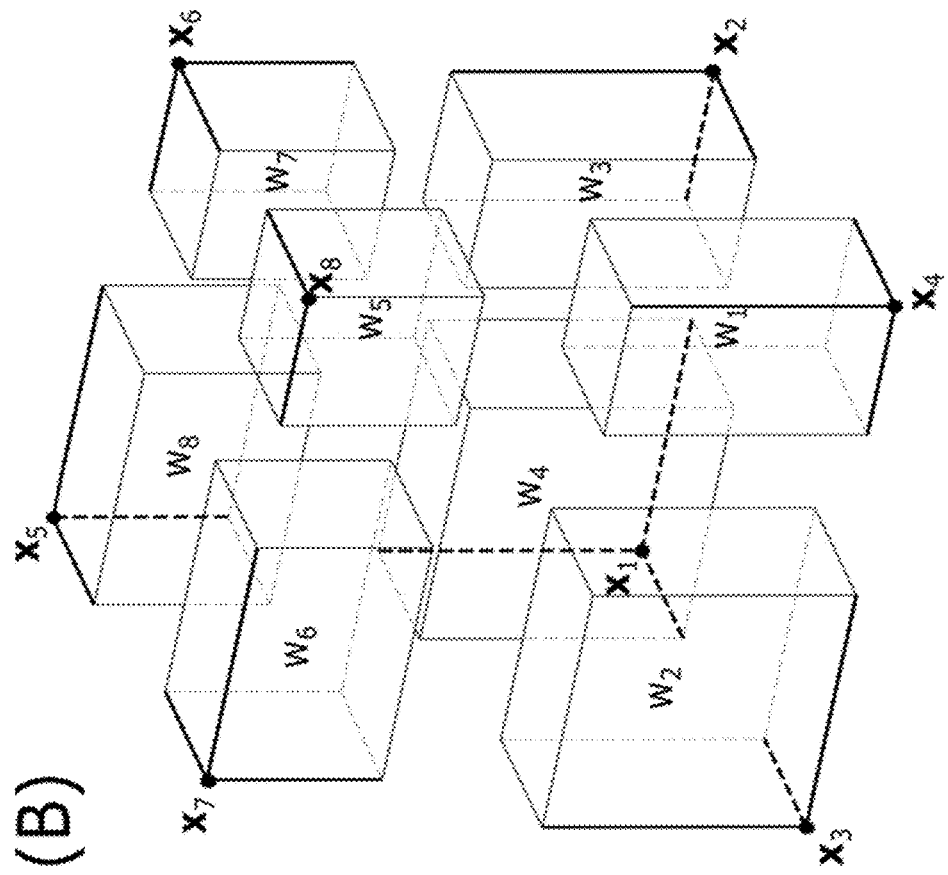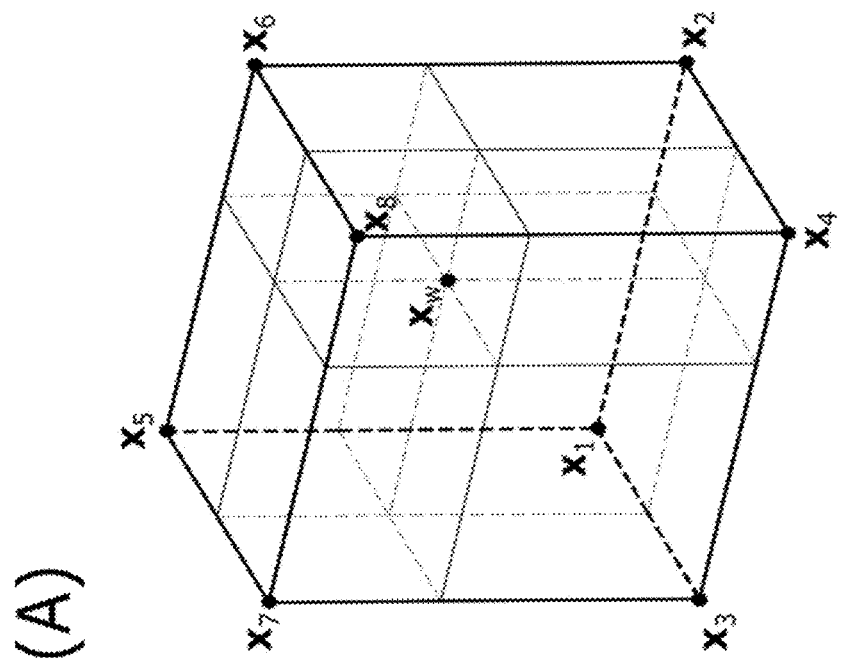
Fig. 19

ULTRASOUND-BASED VOLUMETRIC PARTICLE TRACKING METHOD

INCORPORATION BY REFERENCE TO ANY PRIORITY APPLICATIONS

This application is a continuation-in-part application of U.S. application Ser. No. 14/941,294, filed Nov. 13, 2015, which claims priority to U.S. Provisional Application No. 62/079,834 filed on Nov. 14, 2014; U.S. Provisional Application No. 62/113,929 filed on Feb. 9, 2015; and U.S. Provisional Application No. 62/199,853 filed on Jul. 31, 2015. Any and all applications for which a foreign or domestic priority claim is identified in the Application Data Sheet as filed with the present application are hereby incorporated by reference under 37 CFR 1.57.

BACKGROUND

A two-dimensional echocardiographic particle image velocimetry (PIV) technique introduced in 2010 received much attention in clinical cardiology (Kheradvar, A, et al. (2010) "Echocardiographic particle image velocimetry: a novel technique for quantification of left ventricular blood vorticity pattern" Journal of the American Society of Echocardiography 23(1): 86-94.

Particle image velocimetry (PIV) has been significantly advanced since its conception in early 1990s. With the advancement of imaging modalities, application of 2D PIV has far expanded into biology and medicine. One example is echocardiographic particle image velocimetry that is used for in vivo mapping of the flow inside the heart chambers, which have opaque boundaries. The current trend is to develop three-dimensional velocimetry techniques that take advantage of modern medical imaging tools.

The most commonly used velocimetry techniques to measure optical flows are based on tracing the particles in a fluid flow. Since early 1990s, several algorithms for particle tracking have been developed that are generally referred to particle image velocimetry (PIV). PIV techniques were originally developed based on the snapshots of two- or three-component velocity vector field on a planar cross section of the flow (Westerweel, J. et al. Annual Review of Fluid Mechanics, 2013 45(1): p. 409-436). PIV techniques are evolving with the advancement of software technology, and faster processors as well as technical improvements in imaging hardware. This facilitates the development of new enterprises for measuring the velocity over volumetric domains.

Some of the noteworthy three-dimensional PIV techniques are defocusing PIV (Pereira, F. and M. Gharib Meas Sci Technol., 2002. 13: p. 683-94), holographic PIV (Barnhart, D. H. et al. Applied Optics, 1994. 33(30): p. 7159-7170), Multi-Planar PIV (Falahatpisheh, A. et al. Experiments in fluids, 2014. 55(11): p. 1-15), and Tomographic PIV (Elsinga, G. E., et al. Experiments in Fluids, 2006. 41(6): p. 933-947). The accuracy of the measurement for each 3D PIV method depends on many experimental parameters, particularly on the particle image density, the volume depth, and the type and number of acquisition devices, which make quantitative validation difficult. So far, no 3D PIV challenge has been defined to compare the accuracy of different methods, as previously described for 2D PIV techniques (Stanislas, M., et al. Experiments in Fluids, 2008. 45(1): p. 27-71). However, while the three-dimensional velocity in a particular flow situation is unique, it is anticipated that each 3D PIV technique reports a slightly different vector field. Therefore, there is a need for a platform to systematically validate these methods.

SUMMARY OF THE INVENTION

Some embodiments relate to a method of determining a configuration of constituents in a medium and a rate of motion of the medium, wherein the method includes:
using a volumetric (3D) ultrasound or sonar imaging device to capture ultrasound or sonar images or datasets of at least two volumetric frames of the medium that comprise a change over time in the configuration of the constituents in the medium, wherein the change is related to the rate of motion of the medium;
measuring a field in the at least two volumetric frames;
calculating a 3D velocity vector field for the at least two volumetric frames, using a processor programmed to scale velocities according to voxel size and time gap between volumetric frames,
wherein the 3D velocity vector fields are calculated from the equation relating the configuration of the constituent in the medium to the velocity field by (1):

$$\frac{\partial B}{\partial t} + \vec{v} \cdot \vec{\nabla} B = 0, \tag{1}$$

where B is the acquired brightness scalar field in the region of interest, t is time, $\vec{v}$ is the local 3D velocity vector, and $\vec{\nabla}$ is the gradient operator;
determining the configuration of the constituents in the medium and the rate of motion of the medium from the scaled 3D velocity vector fields; and
displaying an image showing the configuration of the constituents in the medium and the rate of motion of the medium.

In some embodiments, the calculating a 3D velocity vector field for the at least two volumetric frames further comprises interpolating velocities ($v_{x1}$, $v_{x2}$, and $v_{x3}$) of the constituents in the medium for each of the at least two volumetric frames and determining the configuration of the constituents in the medium and the rate of motion of the medium from the interpolated and scaled 3D velocity vector fields.

In some embodiments, the configuration is an arrangement of constituents of the medium.

In some embodiments, the constituents are added to the medium, wherein the added constituents are not intrinsic to the medium.

In some embodiments, the medium is a compressible or an incompressible fluid.

In some embodiments, the field is a brightness field inherent to the medium or its motion.

In some embodiments, the brightness field is inherent to the medium or its motion results from medium natural components.

In some embodiments, the medium natural components are blood components.

In some embodiments, the brightness field is from a tracking agent comprising floating particles detectable in the medium during flow of the medium.

In some embodiments, data are stored in a multidimensional array that represents a quantity in three dimensional space and time.

In some embodiments, the quantity represents brightness field.

In some embodiments, the spatial location of the quantity is known at the time of the acquisition once the data is acquired by the volumetric (3D) ultrasound or sonar imaging device.

In some embodiments, the volumetric (3D) ultrasound or sonar imaging device is a sonar-based device.

In some embodiments, the volumetric (3D) ultrasound imaging device comprises an ultrasound transducer that measures length, width, height and time.

In some embodiments, the data in the multidimensional array are optimized.

In some embodiments, the data are optimized by a method selected from the group consisting of adjusting contrast, adjusting brightness, adjusting sharpness, noise reduction, and motion deblurring of images or datasets.

In some embodiments, motion of the medium or deformation of the medium is detected in open medium space.

In some embodiments, a solid or deformable boundary of the medium is identified and tracked.

In some embodiments, a change in the medium is imposed.

In some embodiments, an improvement in the medium is imposed.

In some embodiments, the solid or deformable boundary of the medium corresponds to a wall enclosing the medium.

In some embodiments, the solid or deformable boundary of the medium is tracked by a method selected from the group consisting of a manual method, a semi-automatic method, and an automatic method.

In some embodiments, the automatic method is selected from the group consisting of multi-planar segmentation, active contour tracking, speckle tracking, machine learning, and artificial intelligence method.

In some embodiments, the change in the medium configuration comprises imposing one or more governing equations of physics to the results.

In some embodiments, the medium is a body of water and the method measures an underwater, three-dimensional flow.

In some embodiments, direction and magnitude of flow velocity are determined within range of a sonar or radar probe.

Some embodiments further include displaying an image showing the solid or deformable boundary of the medium.

In some embodiments, the 3D velocity vector fields are visualized.

In some embodiments, the visualization is done by at least one streamline, pathline, streakline, or particles.

In some embodiments, fluid dynamics-related quantities are derived from the 3D velocity vector fields.

In some embodiments, the 3D velocity vector fields, their properties, or velocity dependent quantities are used for diagnosis, detection of at least one disorder, decision making, or therapeutic purposes.

In some embodiments, the functionality of the medium is assessed based on the 3D velocity vector fields.

In some embodiments, the functionality is expressed in terms of vorticity, kinetic energy, energy dissipation, shear stress, pressure, vortex formation time, or particle residence time.

In some embodiments, the functionality of the deformable body is assessed using the 3D velocity vector fields.

In some embodiments, vortices are imaged using the velocity field.

In some embodiments, the fluid dynamic quantity is pressure or pressure difference.

In some embodiments, equation (1) is solved locally.

In some embodiments, equation (1) is solved globally for an entire configuration field.

In some embodiments, equation (1) is solved by combining local and global methods.

In some embodiments, a configuration of the field is coarsened at least one time.

In some embodiments, the 3D velocity vector fields are solved in at least one coarsened configuration.

In some embodiments, the 3D velocity vector fields are interpolated from at least one coarsened configuration to at least one refined configuration.

In some embodiments, at least one correction velocity field is obtained.

In some embodiments, the correction velocity field is applied to a refined configuration.

In some embodiments, the process of coarsening configurations is repeated.

In some embodiments, the process of interpolating to a finer configuration is repeated.

In some embodiments, the process of obtaining the correction velocity field is repeated.

In some embodiments, the process of applying the correction to the refined configuration is repeated.

In some embodiments, at least one correction field is obtained by using at least one physical constraint.

In some embodiments, equation (1) is expressed in a Cartesian coordinate system:

$$\frac{\partial B}{\partial t} + v_x \frac{\partial B}{\partial x} + v_y \frac{\partial B}{\partial y} + v_z \frac{\partial B}{\partial z} = 0.$$

In some embodiments, equation (1) is expressed in a spherical coordinate system:

$$\frac{\partial B}{\partial t} + v_r \frac{\partial B}{\partial r} + v_\theta \frac{1}{r} \frac{\partial B}{\partial \theta} + v_\varphi \frac{1}{r\sin\theta} \frac{\partial B}{\partial \varphi} = 0.$$

In some embodiments, the physical governing equation is the incompressibility of the medium.

Some embodiments relate to a method of processing three-dimensional images or volumetric datasets to determine a configuration of a medium or a rate of a change of the medium, wherein the method comprises tracking changes of a field related to the medium to obtain a deformation or velocity field in three dimensions.

In some embodiments, the configuration is an arrangement of constituents of the medium.

In some embodiments, the configuration is an arrangement of added constituents to the medium, wherein the added constituents are not intrinsic to the medium.

In some embodiments, the medium is a compressible or an incompressible fluid.

In some embodiments, the field is a brightness field inherent to the medium or its motion.

In some embodiments, the brightness field is inherent to the medium or its motion results from medium natural speckles.

In some embodiments, the medium natural speckles are blood components.

In some embodiments, the brightness field is from a tracking agent comprising floating particles detectable in the medium during flow of the medium.

In some embodiments, data are stored in a multidimensional array that represents a quantity in three dimensional space and time.

In some embodiments, the quantity represents brightness field.

In some embodiments, the spatial location of the quantity is known at the time of the acquisition once the data is acquired by a volumetric (3D) imaging modality.

In some embodiments, the acquired volumetric image(s) is(are) from an acoustic wave-based device.

In some embodiments, the volumetric image modality is a radar-based device.

In some embodiments, the volumetric image modality is a sonar-based device.

In some embodiments, the volumetric imaging modality is a four dimensional ultrasound transducer that measures length, width, height and time.

In some embodiments, the data in the multidimensional array are optimized.

In some embodiments, the data are optimized by a method selected from the group consisting of adjusting contrast, adjusting brightness, adjusting sharpness and noise reduction of images or datasets.

In some embodiments, motion of the medium or deformation of the medium is detected in open medium space.

In some embodiments, a solid or deformable boundary of the medium is identified and tracked.

In some embodiments, a change in the medium is imposed.

In some embodiments, an improvement in the medium is imposed.

In some embodiments, the solid or deformable boundary of the medium corresponds to walls of an enclosing the medium.

In some embodiments, the solid or deformable boundary of the medium is tracked by a method selected from the group consisting of a manual method, a semi-automatic method, and an automatic method.

In some embodiments, the automatic method is selected from the group consisting of multi-planar segmentation, active contour tracking and speckle tracking.

In some embodiments, the change in the medium configuration comprises imposing one or more governing equations of physics to the results.

In some embodiments, the medium is a body of water and the method measures an underwater, three-dimensional flow.

In some embodiments, direction and magnitude of flow velocity are determined within range of a sonar or radar probe.

In some embodiments, the method of processing three-dimensional images or volumetric datasets to determine a configuration of a medium or a rate of a change of the medium comprises:
(a) obtaining at least two volumetric frames that reflect a variation of a medium configuration or its rate of change over time,
(b) calculating a 3D velocity vector field for the at least two volumetric fames, wherein the velocity vector field is calculated based on the fluid equation (2):

$$\frac{\partial B}{\partial t} + v_x \frac{\partial B}{\partial x} + v_y \frac{\partial B}{\partial y} + v_z \frac{\partial B}{\partial z} = 0, \quad (2)$$

(c) interpolating velocities ($v_x$, $v_y$, and $v_z$) in a volumetric frame, (d) scaling final velocity fields according to voxel size and time gap between volumetric frames, and
(e) identifying a solid or deformable boundary of the flow.

In some embodiments, the methods disclosed herein further comprise displaying an image showing a solid or deformable boundary of a medium.

BRIEF DESCRIPTION OF THE DRAWINGS

FIG. 19: Weights. (A) shows the eight nearest neighbors of point $x_2$. (B) illustrates the weights in equation 13, where each volumetric box is isolated from its location in (A) for clarification purposes. Weights are equal to the volume of each box.

DETAILED DESCRIPTION

Figure 1:
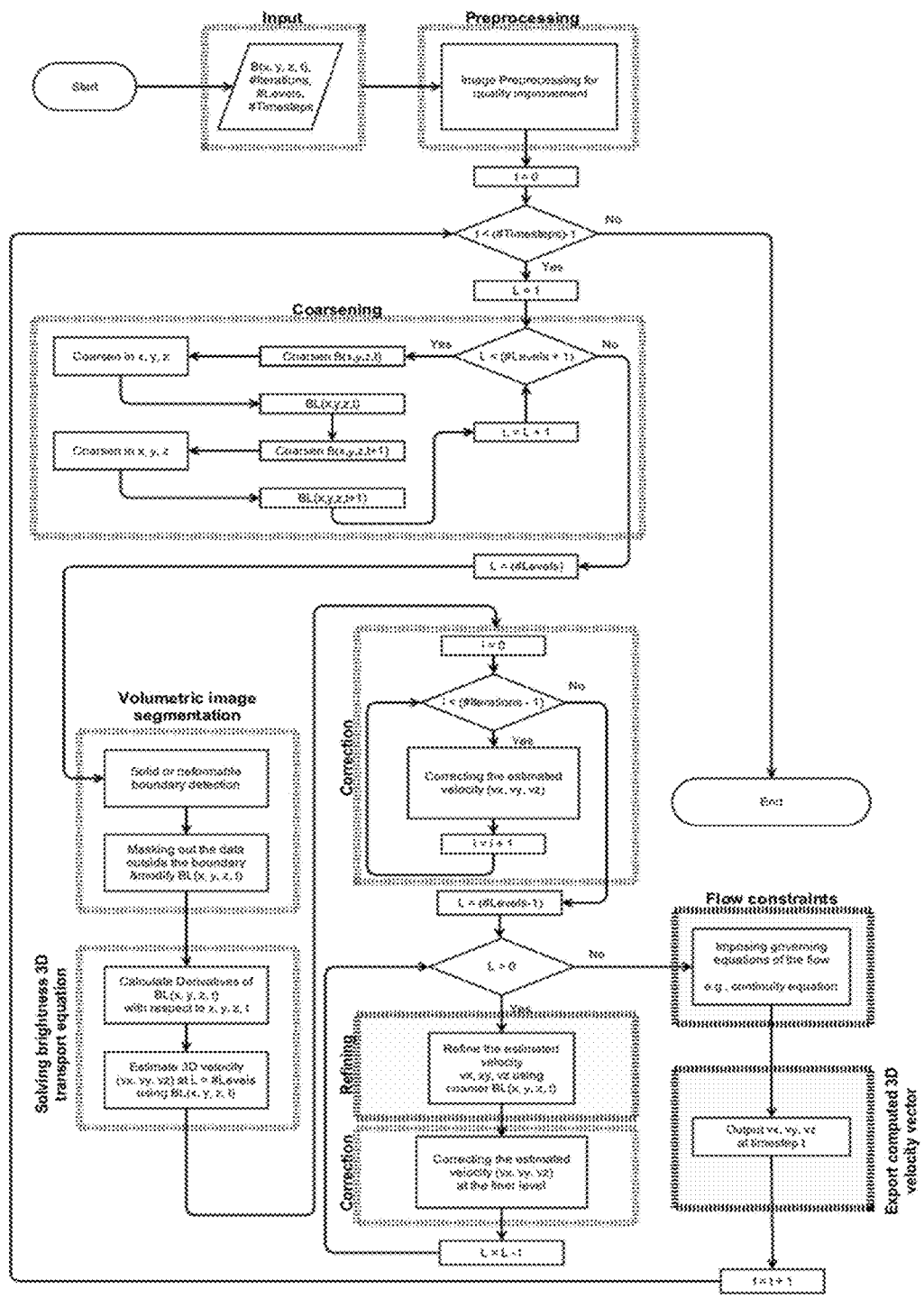
FIG. 1: Flowchart of volumetric echocardiographic particle image velocimetry.

Disclosed is a technique that processes volumetric (3D) images in time to capture the motion of a body of fluid based on tracking/tracing changes in the fluid's brightness field. These changes can be due to inherent patterns in the scattered echo images or from injected particles shining in the flow. This technique processes the brightness information in the flow to obtain the velocity vector field in three dimensions over time.

Data consist of a multidimensional array that stores a quantity, such as the brightness of the fluid tracking agent. These dimensions represent the value of the quantity in three dimensional space and time. The spatial location of the quantity is known at the time of the acquisition, once the data is acquired by a volumetric image modality, such as, but not limited to a 4D ultrasound transducer, there is no need for estimation or computation of the depth or the third component of the coordinate system.

The volumetric frames reflect the variation of the flow field over time.

At least two time frames need to be stored in the above mentioned multidimensional array.

The algorithm includes, but is not limited to, solving a transport equation of brightness and correlation techniques. The algorithm uses the following steps:

Step 1

The process starts by inputting a multi-dimensional array and specifying a 3D window size (W×W×W), the number of levels (L) that the frames will be coarsened and refined in three coordinates, such as, but not limited to x, y, z, and the number of iteration(s) (N) for correcting the estimated 3D velocity vectors.

Step 2

The multidimensional array can be pre-processed for a better outcome, such as, but not limited to adjusting contrast, brightness, sharpness and noise reduction.

Step 3

Coarsening is done by applying a one dimensional filtering, such as, but not limited to Gaussian filtering to every other voxel along the first spatial dimension, then using the resulting frame and applying another one dimensional filter, such as, but not limited to Gaussian filtering to every other voxel in the second spatial dimension, the resulting frame and applying another one dimensional filter, such as, but not limited to Gaussian filtering to every other voxel in the third spatial dimension. This coarsening generates a volumetric frame with half the resolution.

Step 4

The processing of the volumetric frames is done by considering one pair of frames (Vol1 and Vol2): timestep at t and a next timestep at t+1.

Step 5

In one aspect of the algorithm, the volumetric frames (Vol1 and Vol2) are reduced to half the number of voxels in all three dimensions, depending on the number of levels given.

Step 6

The derivative of the brightness is calculated with respect to three dimensions and frames (t) for each voxel for the coarsest level L.

Step 7

Based on the calculated derivatives in step 5, the transport equation of brightness in any three dimensional coordinate system, such as, but not limited to Cartesian coordinates is solved in two windows of size W×W×W voxels in $Vol_1$ and $Vol_2$ in three dimensional space. The transport equation represents the total change of brightness both temporally and spatially. These two windows are at location (i,j,k) in both Vol1 and Vol2.

$$\frac{\partial B}{\partial t} + v_x \frac{\partial B}{\partial x} + v_y \frac{\partial B}{\partial y} + v_z \frac{\partial B}{\partial z} = 0 \quad (2)$$

Step 8

The velocity vector, $V=(v_x, v_y, v_z)$, resulting from the above equation is corrected in a window of smaller size $W_1 \times W_1 \times W_1$, ($W_1 < W$). However, the window in $Vol_2$ is translated in 3D based on the estimated velocity for the window. Equation (2) is solved in the smaller windows to find the corrections, $V_C$, then V is updated by:

$$v_x = v_x + v_{xC} \quad (3)$$

$$v_y = v_y + v_{yC} \quad (4)$$

$$v_z = v_z + v_{zC} \quad (5)$$

Step 9

After finding the velocity in the coarsest level, the velocities $(v_x, v_y, v_z)$ are interpolated in a volumetric frame where its resolution is double that of the coarser frame. This is done by applying a one dimensional filter, such as, but not limited to a Gaussian filter to a volumetric frame double the size of the coarser frame in the first spatial dimension, then using the resulting frame and applying a one dimensional filter, such as, but not limited to a Gaussian filter to a volumetric frame double the size of the coarser frame in the second spatial dimension, then applying a one dimensional filter, such as, but not limited to a Gaussian filter to a volumetric frame double the size of the coarser frame in the third spatial dimension.

Step 10

Step 6 is repeated for this finer volumetric frame to correct the velocities.

Step 11

Steps 4-8 are repeated until all the levels are computed.

Step 12

Steps 2-9 are repeated until all the time steps are computed.

Step 13

Final velocity fields are scaled according to voxel size and time gap between volumetric frames.

Step 14

The solid boundary of the flow (e.g., left ventricular endocardium), are identified and tracked and are augmented to the results, such as, but not limited to visualization or flow improvement. Tracking of the solid boundary is done manually, semi-automatically, or by automatic methods, such as, but not limited to multiplanar segmentation, active contour tracking and speckle tracking.

Step 15

The flow improvement includes, but is not limited to, imposing governing equations of the flow to the results, which is obtained as explained above, such as but not limited to the continuity equation of the flow.

A flowchart of volumetric echocardiographic particle image velocimetry is depicted in FIG. 1.

Figure 2:
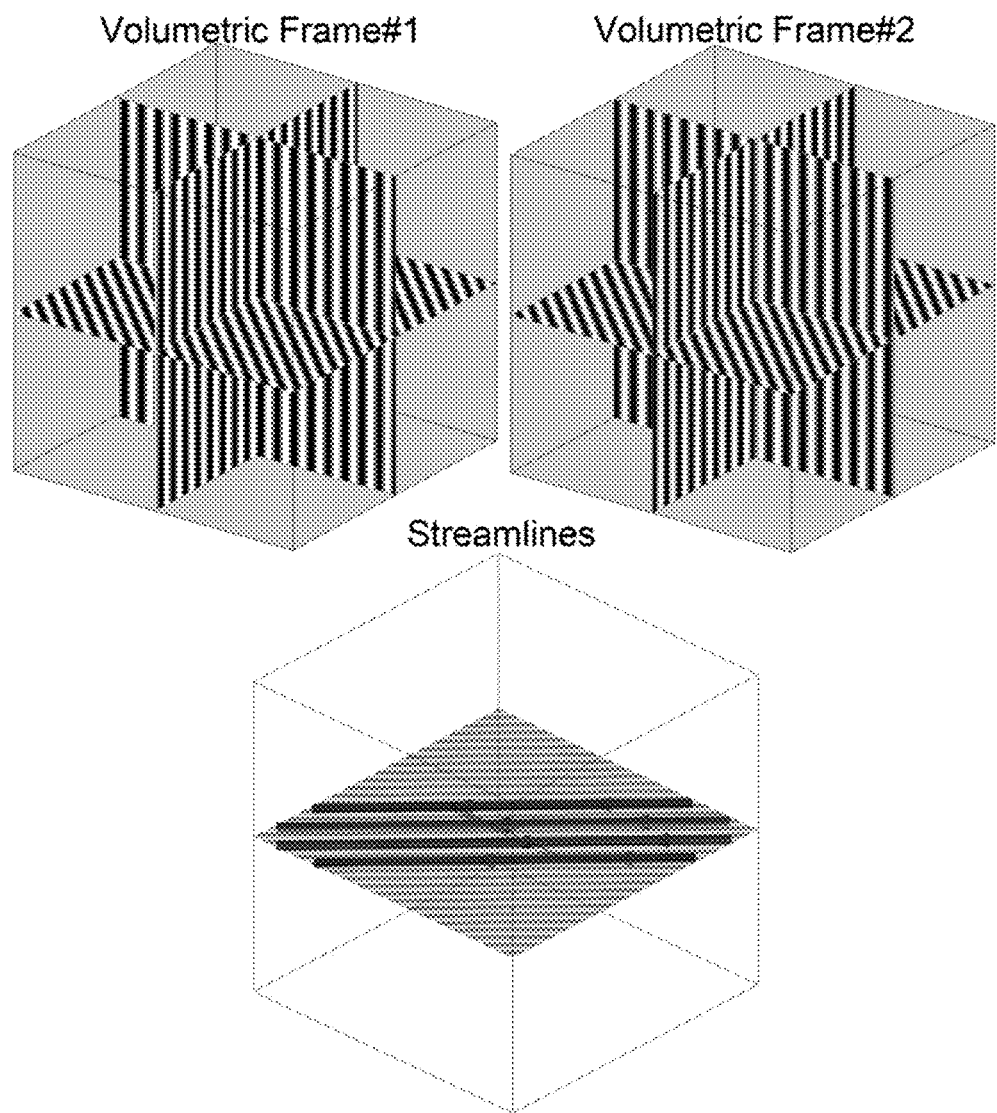
FIG. 2: In-plane sinusoidal wave in three dimensional space.

We generated a 3D sinusoidal wave as follows for the purpose of validation, which is based on the superposition of three sinusoidal plane-waves:

$$\sin(\varkappa_1 x + \omega_1 t) + \sin(\varkappa_2 x + \omega_2 t) + \sin(\varkappa_3 x + \omega_3 t) \quad (6)$$

where $$\kappa_i = \begin{bmatrix} K_x \\ K_y \\ K_z \end{bmatrix}_i$$

is the spatial frequency or wavelength in three dimensions and $\omega_i$ is the angular frequency. An in-plane sinusoidal wave in three dimensional space is depicted in FIG. 2.

Figure 3:
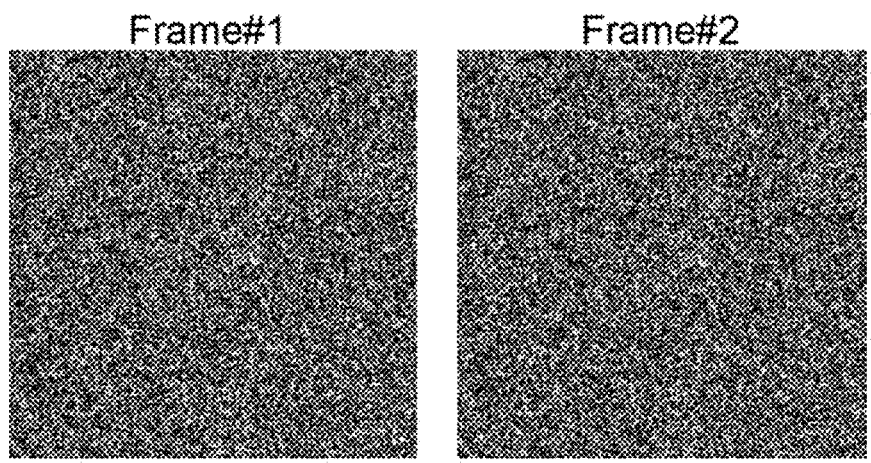
FIG. 3: The two frames used to compute the experimental strong vortex. The vortex was extended in three different orientations for validation of VE-PIV.
Figure 4:
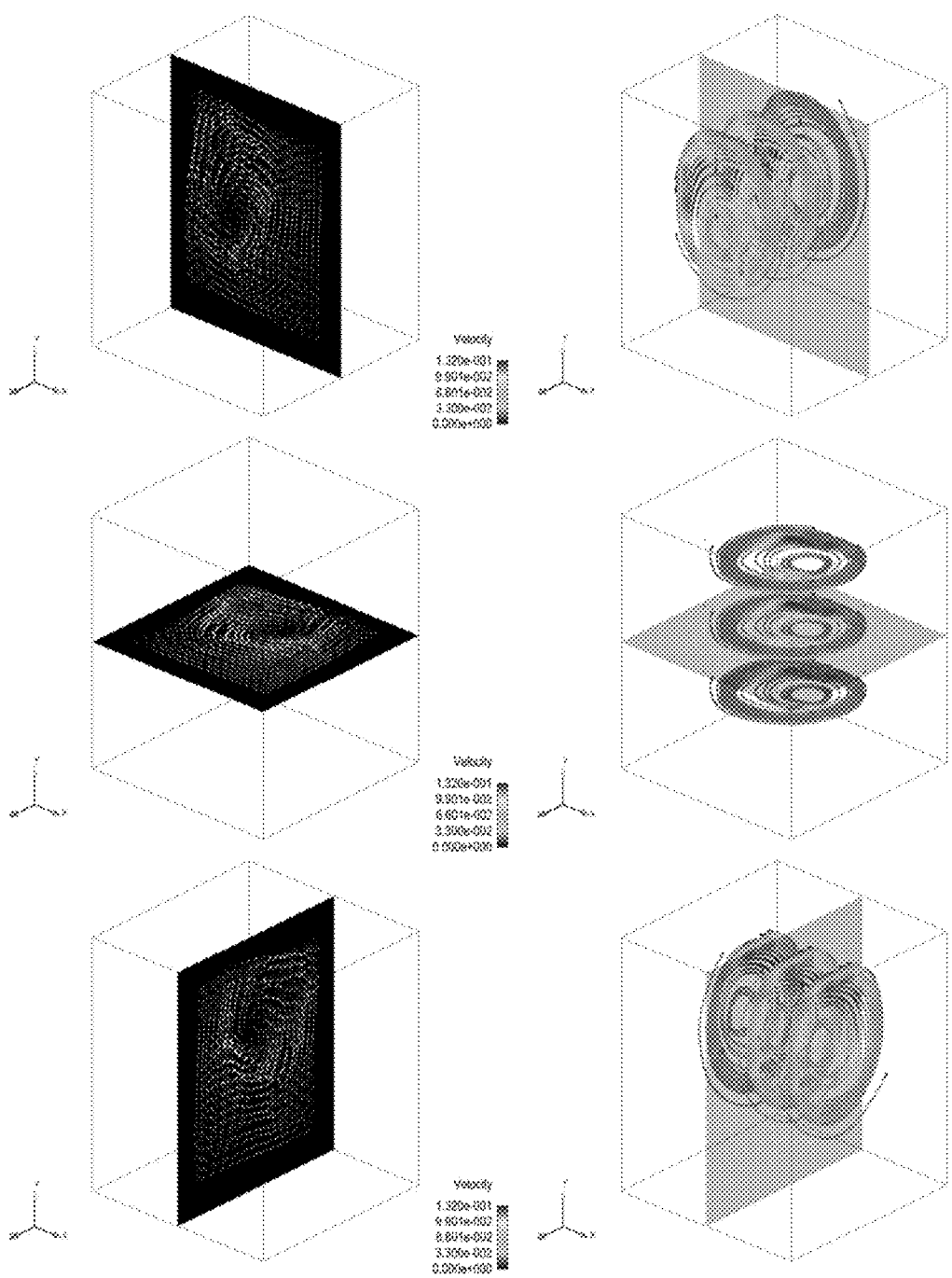
FIG. 4: The results of VE-PIV for the experimental strong vortex in three different orientations.
Figure 5:
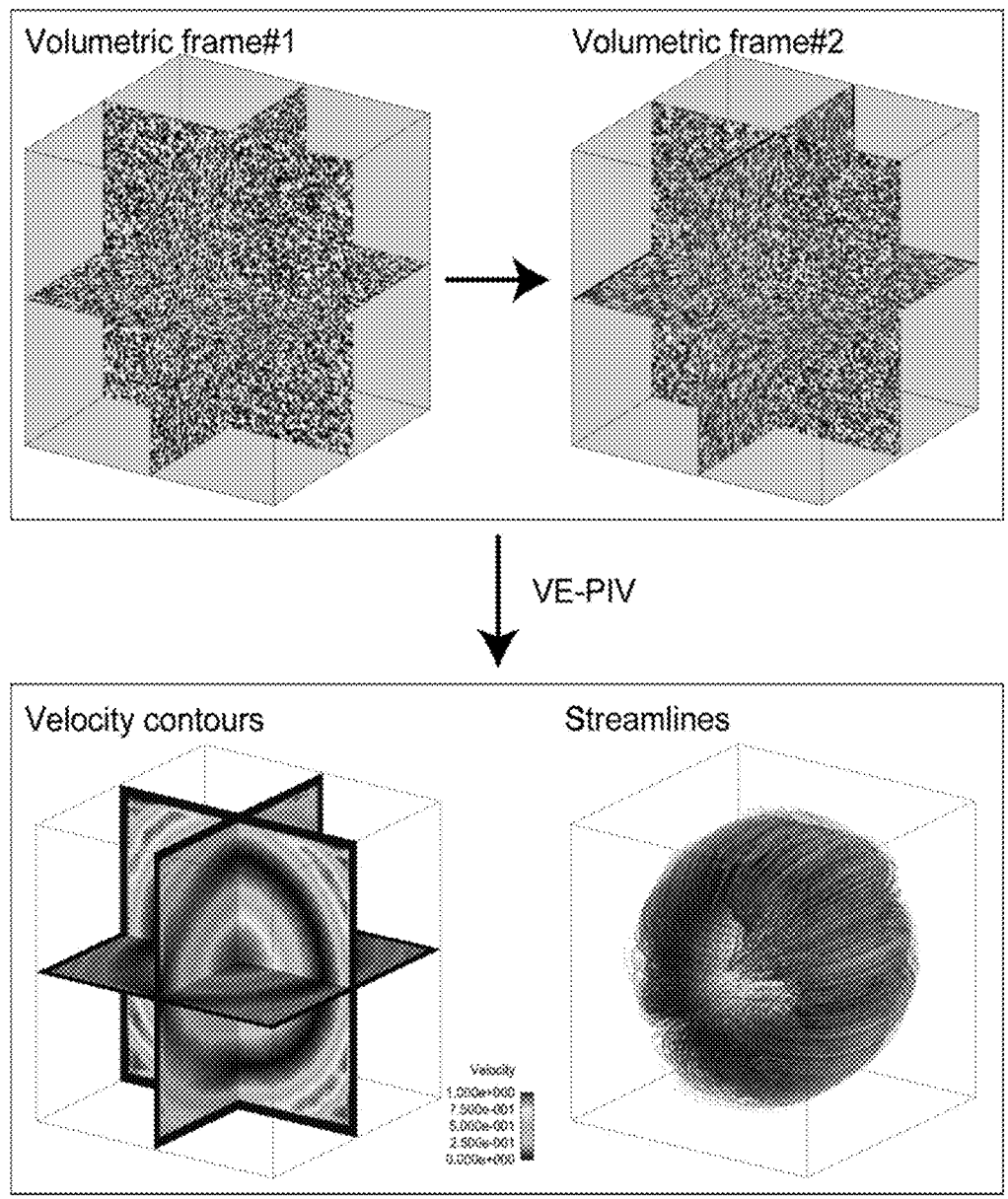
FIG. 5: The generated brightness fields, velocity contours, and streamlines of a Hill's Spherical Vortex (HSV). Volumetric frame#2 is generated by using a 3D random field (Volumetric frame#1) and a known velocity field, which was chosen to be a Hill's Spherical Vortex (Hill, M. J. M., On a Spherical Vortex. Proceedings of the Royal Society of London, 1894. 55(331-335): p. 219-224).

For the process of validation, a method was developed to create three dimensional brightness field using a given velocity field (FIG. 4). Using this method, two volumetric frames are created (FIG. 3). After applying a three dimensional velocity field to a random field (considered the brightness field), the method results in a new volumetric frame. In other words, if these two volumetric frames are processed by VE-PIV, the prescribed 3D velocity field is obtained. The algorithm for generating a 3D brightness field given a velocity field is given above. Example generated brightness fields, velocity contours and streamlines of a Hill's Spherical Vortex (HSV) are shown in FIG. 5.

Conservation of Brightness

The 3D brightness field, B, can be considered a conserved quantity when the time interval between two frames are sufficiently small. The amount of brightness that exists in the first frame remains conserved in the second frame and is dependent on the local velocity field. Mathematically, this implies that the total derivative of the brightness field must vanish locally:

$$\frac{\partial B}{\partial t} + \vec{v} \cdot \nabla B = 0. \quad (1)$$

where:
B is the acquired brightness scalar field in the region of interest, t is time, $\vec{v}$ is the local 3D velocity vector, and $\vec{\nabla}$ is the gradient operator.

Depending on the configuration of the device for acquiring the brightness field, one can use a Cartesian or a spherical coordinate system. The conservation of brightness can be expressed in a Cartesian coordinate system as:

$$\frac{\partial B}{\partial t} + v_x \frac{\partial B}{\partial x} + v_y \frac{\partial B}{\partial y} + v_z \frac{\partial B}{\partial z} = 0$$

or in a spherical coordinates system by:

$$\frac{\partial B}{\partial t} + v_r \frac{\partial B}{\partial r} + v_\theta \frac{1}{r} \frac{\partial B}{\partial \theta} + v_\varphi \frac{1}{r \sin\theta} \frac{\partial B}{\partial \varphi} = 0.$$

Volumetric Echocardiographic Particle Image Velocimetry

Some embodiments relate to an ultrasound-based, volumetric echocardiographic particle image velocimetry technique that robustly acquires blood flow dynamics in three spatial dimensions and in real time using blood natural speckles, without any need for intravenous (IV) contrast. This method is termed "Volumetric Echocardiographic Particle Image Velocimetry (V-Echo-PIV)."

Example 1

Contrast Agent-Free Volumetric Echocardiographic Particle Image Velocimetry (V-Echo-PIV)

Currently, modern echocardiography systems are equipped with matrix array probes with 3D acquisition capability. However, this feature has not yet been employed for 3D vector characterization of blood flow and is only used for either structural analyses or 3D color Doppler flow, which does not yield a velocity vector field. Here, we introduce a method that generates a velocity vector field in 4D (3D space and time) based on volumetric echocardiographic images, without any need for a contrast agent.

Methods

We developed an in-house computer program that processes volumetric echocardiographic images by solving the transport equation of brightness field in 3D over time and computes 3D velocity vector field. Instead of using a contrast agent, blood speckles are used as tracer particles for in-vivo data provided by GE Vingmed Ultrasound. The brightness transport equation was solved in a least square sense, using proper interrogation window sizes in consecutive volumetric frames.

For validation, a method was developed for creating brightness fields by using given 3D velocity fields. As a test for predicting complex 3D rotational flows, several synthetic volumetric brightness fields were generated and processed. After development and validation, volumetric echo images in an adult healthy human left ventricle were processed. This set of 3D images were acquired without using a contrast agent by a 4V GE ultrasound matrix array transducer, with temporal resolution of 21.5 milliseconds and a voxel size of 0.9×0.6×0.9 mm³.

Results

Figure 6:
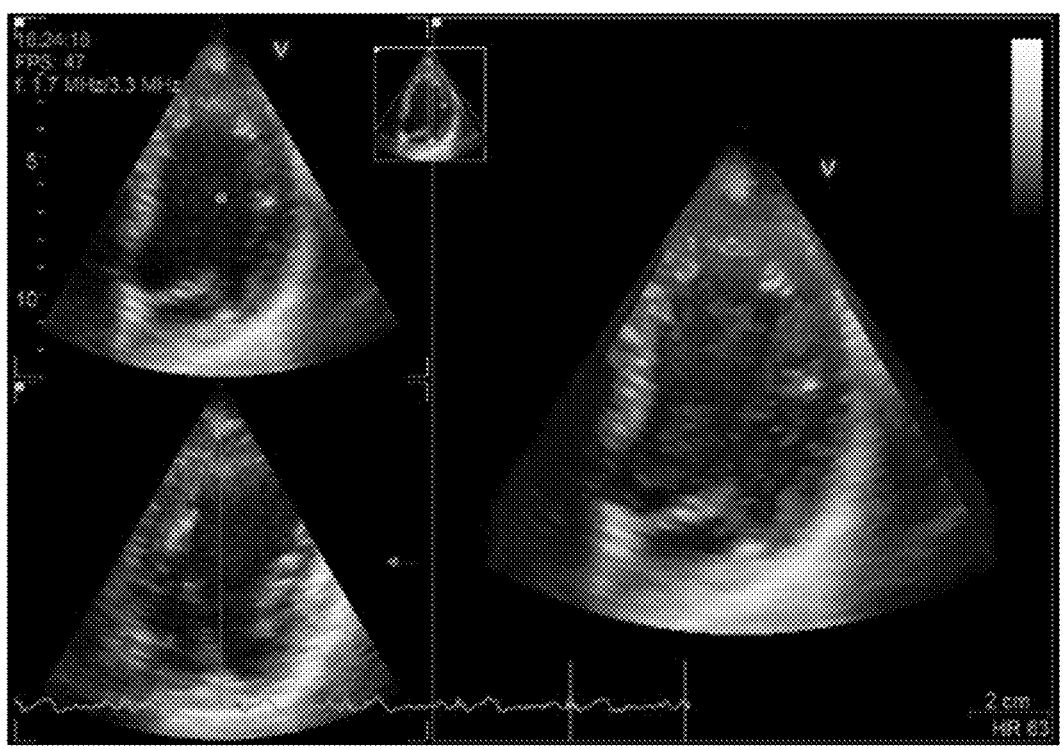
FIG. 6: The snapshot of the VolDICOM of the data during early systole. Mitral valve is closed. No contrast agent was used during the acquisition.
Figure 7:
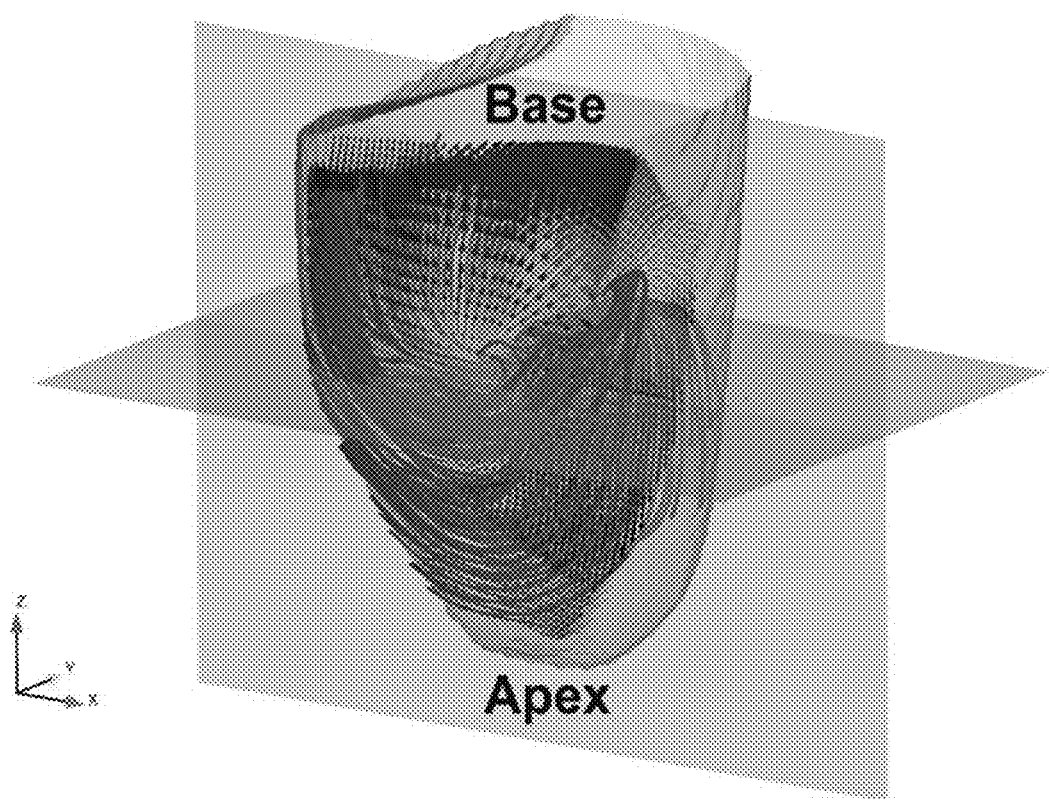
FIG. 7. The velocity vector processed by VE-PIV in early systole overlaid with streamlines and the LV border. The illustrated velocity vectors are in a plane located in the center of the chamber coincident with the center of flow rotation. The rotational flow, shown by streamlines, circulates inside the LV and begins to exit the chamber through the aortic valve. The swirling momentum, which was created during diastole due to the transmitral jet and the LV wall, transfers the momentum from the LV to the LV outflow tract.

The expected velocity fields were successfully predicted by VE-PIV in all the synthetic cases. FIG. 6 illustrates a snapshot of the VolDICOM of the raw data before processing with VE-PIV. FIG. 7 illustrates the results of VE-PIV, including the LV wall, velocity vector and rotational streamlines in the early systole inside the left ventricle.

This method characterizes blood flow in 3D, based on contrast agent-free volumetric images of human heart. Contrast agent-free V-Echo-PIV is a method that provides three-dimensional flow data without inconvenient injection of contrast agent. This method is particularly advantageous for studies that involve the pediatric population, where safety and effectiveness of contrast agents are not yet established.

Example 2

Association Between Right Ventricular Flow and Strain in Patients with Right Ventricular Dysfunction Right ventricular (RV) flow and its connection to RV strain and strain rate in patients with systolic RV dysfunction due to pulmonary hypertension are studied. The results are compared to data from age- and gender-matched control healthy subjects. This work uses our three-dimensional (3D) echocardiographic particle image velocimetry (Echo-PIV) tool, in addition to advanced 3D strain imaging to assess the right heart.

To date, flow inside the left heart has been extensively investigated with both in vitro and in vivo imaging. However, very little quantitative information is available regarding blood flow inside the right heart. More specifically, no study has yet addressed the development of the flow field during the progression of RV dysfunction, despite the fact that RV failure may carry a worse prognosis than left ventricular (LV) failure. Particular reasons for the lack of this knowledge are: (1) because the RV is wrapped around the LV, its non-symmetric, crescent shape limits 2D echocardiographic flow evaluations; and (2) due to the instability of the forming RV vortex, which interacts with the surrounding walls, highly time-dependent RV flow limits Magnetic Resonance Imaging (MRI) to capturing only relatively large-scale flow structures, while effective phase averaging over several cardiac cycles prevents imaging of local flow instabilities. Additionally, although LV strain analysis is a commonly used clinical parameter, to date the use of RV strain has been purely experimental, and no clinical consensus exists on its proper use. Therefore, it is still unknown whether flow changes in RV are sensitive to the signs of early-stage RV dysfunction reflected in myocardial contractile function. We hypothesized that the 3D flow field inside the RV could be correlated with myocardial function represented by RV strain and strain rate, and that quantifying this relationship provides a basis to devise diagnostic indices to detect and characterize RV dysfunction.

We have developed a 3D Echo-PIV module based on real time reconstruction of the flow-field. Using this new technique, we determine how the 3D RV flow field changes in RV dysfunction, and whether these changes are correlated with changes in RV strain and/or strain rates. This information provides a basis for earlier (or more efficient) diagnosis of RV dysfunction, including latent RV dysfunction in asymptomatic patients.

We quantify the 3D flow field of the right ventricle in patients with RV systolic dysfunction, due to pressure overload as a result of pulmonary hypertension. All results are compared with results of patients with normal RVs.

The flow field inside the right heart of patients with RV dysfunction is studied using 3D Echo-PIV and compared with age- and gender-matched control subjects. Comparison with 4D Flow MR is used to validate the large-scale flow features. This quantitatively identifies the pathologic flow features related to RV dysfunction due to pressure overload.

We obtain 3D speckle tracking-derived RV strain and strain rates in patients with RV systolic dysfunction due to pulmonary hypertension and in control patients. We test whether the strain results can be correlated with the previously obtained 3D flow fields from the RVs.

Strain imaging is a powerful diagnostic tool that has yet to realize its full potential, particularly in the RV. Comparing RV strain and RV strain rate to flow allows quantitative identification of pathologic flow and RV strain features related to RV dysfunction and the relationship of these independent indicators of RV function to each other.

We devise novel diagnostic indices to detect and characterize RV dysfunction based on the acquired 3D flow fields.

These studies extend echocardiographic-based vortex imaging to the right heart to test whether RV flow features such as vortex formation can be correlated to RV strain and strain rate in RV dysfunction and whether it is possible to define diagnostic measures for early-stage dysfunction according to the data from RV flow and RV strain analyses.

Current diagnostic technologies make it extremely challenging to evaluate RV function, mainly because of the RV's complex geometry, the limited definition of RV endocardial surface caused by the heavily trabeculated myocardium, the RV's retrosternal position, which permits only limited 2D echocardiographic imaging windows, and the marked load dependence of current RV function indices (Rudski L G et al. Journal of the American Society of Echocardiography 2010; 23:685-713; Silverman N H et al. Pediatr Cardio. 1983; 4:197-204; Levine R A et al. Circulation. 1984; 69:497-505; and Leeuwenburgh B P J et al. American Journal of Physiology—Heart and Circulatory Physiology. 2002; 282: H1350-H1358). Clinical assessment of RV dysfunction is equally difficult, as most patients have no clinical signs of systemic venous congestion until the late stages (Tayyareci Y et al. Eur J Echocardiogr. 2008; 9:516-521; Bleasdale R A et al. Heart. 2002; 88:323-324; La Vecchia L et al. American heart journal. 2001; 142:181-189 and Nakamura S et al. American heart journal. 1994; 127:49-55). Our results demonstrate that vortex imaging and right ventricular strain are technologies that provide a basis for improved echocardiographic-based RV assessment, since they provide quantitative information about RV flow and contractile state that are not currently used for diagnosis of RV dysfunction.

Echocardiographic Particle Image Velocimetry and Vortex Imaging

Figure 8:
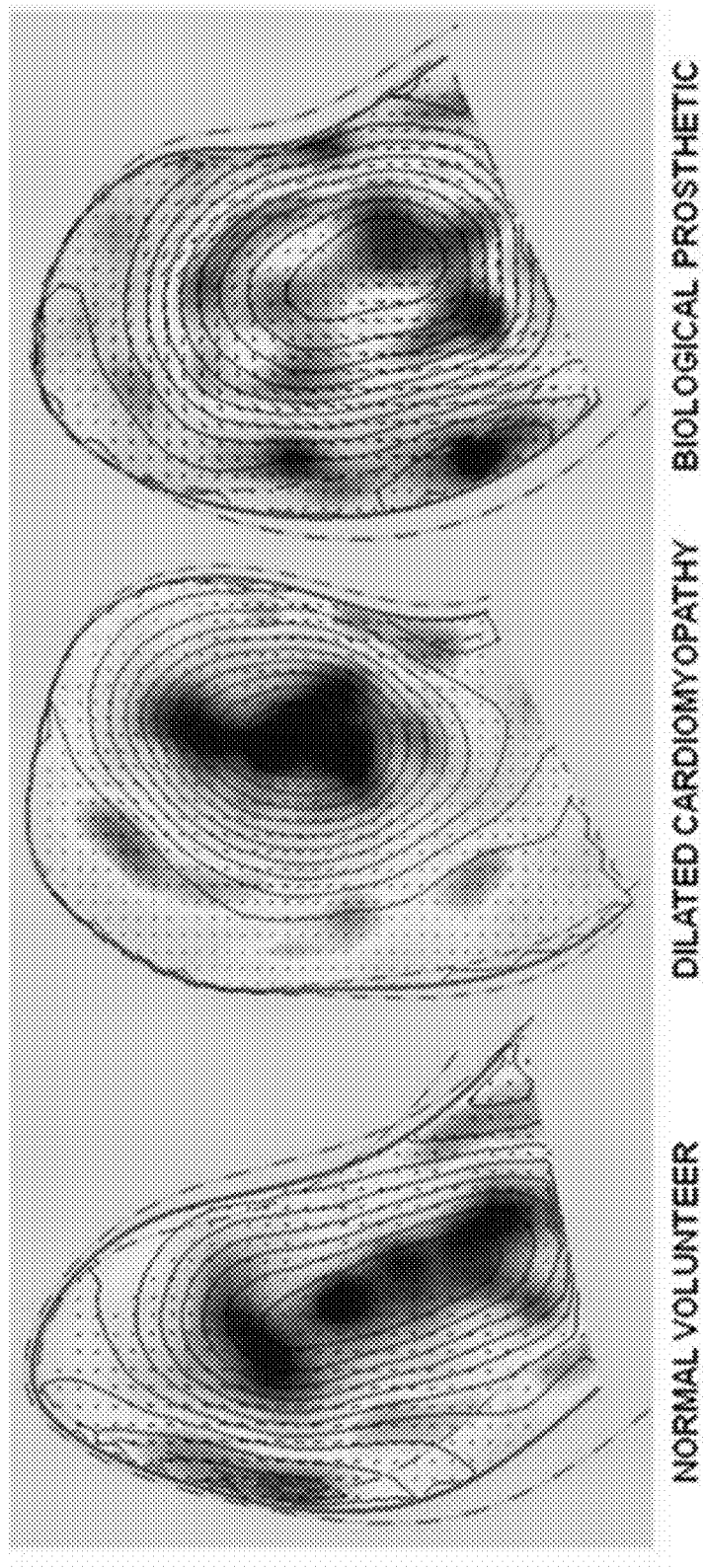
FIG. 8. 2D Echo-PIV's steady streaming intraventricular flow: (left) in a healthy volunteer's LV; (middle) in an LV with dilated cardiomyopathy; (right) in an LV with a bioprosthetic mitral valve. Pictures correspond to Apical 3Ch projection; shading represents circulatory pattern, dark gray/black is clockwise rotation, and light gray is counter-clockwise rotation (Kheradvar A et al. J Am Soc Echocardiography 2010; 23:3102-3111).

Recently, progress has been made to incorporate quantitative fluid dynamics into echocardiography using particle tracking algorithms (Kim H B et al. Exp Fluids. 2004; 36:455-462; Zheng H et al. Applied Physics Letters. 2006; 88:261915) that are based mostly on the well-known optical imaging technique of Particle Image Velocimetry (PIV) (Adrian R J et al. Annual Review of Fluid Mechanics. 1991; 23:261-304; Willert C E et al. Exp Fluids. 1991; 10:181-193). PIV began as an optical method for fluid visualization to obtain instantaneous velocity measurements and related properties in the fluids. In this technique, the fluid is seeded with tracer particles, which are assumed to faithfully follow the dynamics of flow. The motion of these seeding particles is used to compute the flow's velocity. The application of the PIV method to images obtained by ultrasound was first reported by Crapper et al., who used a medical ultrasound scanner to image kaolin particles in a study of sediment-laden flows (Crapper M et al. Dynamics of Atmospheres and Oceans. 2000; 31:233-245). In its current form, 2D ultrasound-based PIV or 2D Echo-PIV was introduced by Kim et al., through capturing digital B-mode images of contrast agent particles (Kim H B et al. Exp Fluids. 2004; 36:455-462), and has been further used for vortex imaging by Kheradvar et al. (FIG. 8) (Kheradvar A et al. J Am Soc Echocardiogr. 2010; 23:3102-3111). This technique computes the velocities of the ultrasound-imaged particles based on the PIV technique, with $\Delta t$ being equal to scanning time. The number of beams and the samples along each beam define the number of pixels for each image after scan conversion. Particles used as the flow tracers are microbubbles filled with octafluoropropane encapsulated in either a lipid (DEFINITY®, Lantheus Medical Imaging, Inc.) or protein (Optison™, GE Healthcare) outer shell (Zheng H et al. Applied Physics Letters. 2006; 88:261915; Liu L L et al. Phys. Med. Biol. 2008; 53:1397-1412), which are both FDA-approved for clinical use. This technique allows the velocity directions and streamlines, principal blood flow patterns, recirculation regions, and vortices to be drawn with reasonable confidence in a reproducible scheme (Kheradvar A et al. J Am Soc Echocardiogr. 2010; 23:3102-3111). Echo-PIV has been found to be a promising approach, and the results obtained appear to be quantitatively meaningful (Kheradvar A et al. J Am Soc Echocardiogr. 2010; 23:3102-3111; Sengupta P P et al. JACC: Cardiovascular Imaging. 2012; 5:305-316; and Hong G-R et al. JACC: Cardiovascular Imaging. 2008; 1:705-717). Kheradvar et al. have shown that Echo-PIV can define the major flow features, circulation regions, and vortices in a reproducible scheme (Kheradvar A et al. J Am Soc Echocardiogr. 2010; 23:3102-3111). In recent years 2D Echocardiographic-PIV (Echo-PIV) has received enormous attention in the clinical setting, mainly due to its quantitative capacity for assessing left ventricular (LV) blood flow (FIG. 8) (Sengupta P P et al. Journal of the American College of Cardiology. 2007; 49:899-908; Hong G-R et al. J Am Coll Cardiol Img. 2008; 1:705-717; Kheradvar A et al. Journal of American Society of Echocardiography. 2010; 23:86-94; Kheradvar A et al. Journal of the American Society of Echocardiography 2012; 25:220-227; Eriksson J et al. American Journal of Physiology-Heart and Circulatory Physiology. 2011; 300:H2135-H2141; Garcia D et al. IEEE Transactions on Medical Imaging. 2010; 29:1701-1713; Luo J et al. Ultrasound in Medicine and Biology. 2011; 37:980-995; Pedrizzetti G et al. Annals of biomedical engineering. 2010; 38:769-773; Zhang F et al. Ultrasound in Medicine and Biology. 2011; 37:450-464 and Agati L et al. European Heart Journal—Cardiovascular Imaging. 2014).

Recent advances in understanding LV fluid dynamics based on experimental (Kheradvar A et al. ASAIO J. 2006; 52:34-38; Domenichini F et al. J Biomech. 2007; 40:1988-1994; Kheradvar A et al. Annals of biomedical engineering. 2009; 37:1-13; Kheradvar A et al. ASAIO J. 2007; 53:8-16 and Pedrizzetti G et al. Annals of biomedical engineering. 2014:1-15) and numerical simulations (Domenichini F et al.

J Fluid Mech. 2005; 539:179-198; Pedrizzetti G et al. Physical Review Letters. 2005; 95:108101 and Schenkel T et al. Annals of biomedical engineering. 2007; 37:503-515) have shed light on many aspects of ventricular flow, such as the development of intraventricular vortices. These vortices are shown to significantly influence trans-mitral momentum transfer and help redirect the flow from the left atrium toward the aortic outlet via LV (Kheradvar A et al. Journal of the American Society of Echocardiography 2012; 25:220-227; Panupong J et al. Journal of the American Society of Echocardiography 2009; 22:427-431). Alternatively, formation of unnatural vortices can be a sign of adverse blood flow, which can be a sign of progressive LV dysfunction (FIG. 8) (Kheradvar A et al. Journal of American Society of Echocardiography. 2010; 23:86-94; Kheradvar A et al. Journal of the American Society of Echocardiography 2012; 25:220-227; Kheradvar A et al. Journal of the American College of Cardiology. 2008; 51:A104; and Pedrizzetti G et al. Nat Rev Cardiol. 2014; 11:545-553). The knowledge gained about LV fluid dynamics, and in particular those associated vortical flow motion, has introduced novel clinical indicators for LV function based on vortex dynamics (Hong G-R et al. J Am Coll Cardiol Img. 2008; 1:705-717; Kheradvar A et al. Journal of the American Society of Echocardiography 2012; 25:220-227; Gharib M et al. Proc Natl Acad Sci. 2006; 103:6305-6308; Poh K K et al. European Journal of Echocardiography. 2011; and Belohlavek M. European Heart Journal—Cardiovascular Imaging. 2012). The process of vortex formation is peculiar in the RV, as it is subjected to instabilities induced by the asymmetric surrounding geometry. However, no quantitative information currently exists on how development of these vortices would potentially affect RV function.

We have extended 3D echocardiographic-based vortex imaging and strain imaging to the right heart to test whether the RV flow field can be correlated to RV dysfunction in the same way previously described for the left ventricle (Kheradvar A et al. Journal of the American Society of Echocardiography 2012; 25:220-227) and whether we can define diagnostic measures for early-stage dysfunction based on RV flow and strain imaging.

Development of 3D Echo-PIV

For the first time, we have developed and validated a 3D Echo-PIV software that works based on two independent concepts: (1) multi-planar reconstruction of the 2D velocity vector fields, and (2) direct volumetric acquisition. 3D Echo-PIV uses ultrasound beams as the imaging source for visualizing blood flow within the opaque cardiac chambers.

Figure 9:
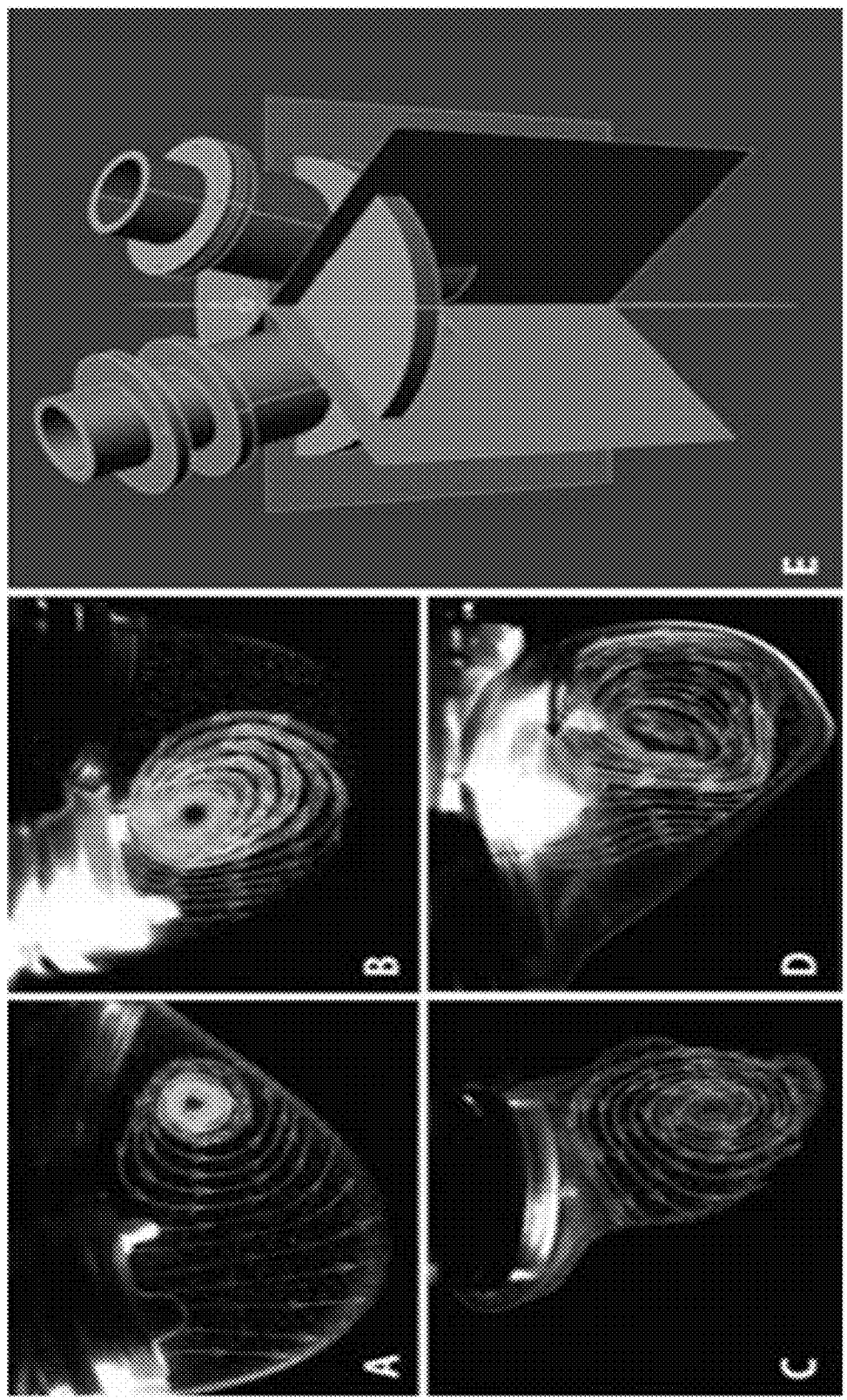
FIG. 9: Vortex formation inside a transparent model of the right ventricle. The streamlines are shown based on the velocity data obtained through multiplanar PIV. (A)-(D) show a vortex formed proximal to the RVOT at different angles with respect to the camera; (A) 0 degrees; (B) 45 degrees; (C) 90 degrees; (D) 135 degrees. (E) The locations of laser sheets with respect to inflow/outflow sections of the heart pulsed flow simulator. RVOT: right ventricular outflow tract; DPIV: Digital Particle Image Velocimetry (Falahatpisheh A et al. Exp Fluids. 2014; 58: 1848).

Multiplanar 3D Flow Reconstruction 3D flow reconstruction is performed by carefully assembling all the velocity information at multiple perpendicular 2D velocity fields. To achieve this, we developed an in-house code in C++ whose tasks are summarized here. The algorithm reads, sorts, and assembles all the velocity data of multiple perpendicular fields obtained from any PIV modality. To implement and validate the algorithm, we first acquired the data in vitro using the heart-pulse duplicator (Falahapisheh A et al. European Journal of Mechanics—B/Fluids. 2012; 35: 2-8). The experimental system enables meticulous control of the flow-rate and validation of the method. Simultaneous multiple 2D acquisitions were performed in real time for 3D reconstruction. 2D PIV captures in-plane velocity components in a slice of the domain (FIG. 9). Four perpendicular planes were employed for 3D reconstruction of the RV flow field. For each plane, the velocity vectors were calculated based on optical flow techniques (Baraldi P et al. Biomedical Engineering, IEEE Transactions on. 1996; 43:259-272; Barron J L et al. International Journal of Computer Vision. 1994; 12:43-77 and Beauchemin S S et al. ACM Computing Surveys (CSUR). 1995; 27), which are based on finding the displacement vector that maximizes the correlation between the corresponding regions of interest (ROIs) in two consecutive frames. The results measure the displacement and velocity vectors of the illuminated microbubbles in all ROIs within each image.

To improve the interpolation's accuracy and minimize its error, the interpolated velocity field should be closely matched with the physical values that satisfy the flow governing equations. Since the interpolated velocity field does not necessarily satisfy the incompressibility condition of the flow in 3D, the field needs to be modified accordingly. In this regard, an irrotational velocity field whose divergence cancels out the divergence of the interpolated velocity field is added to it (Falahatpisheh A et al. Exp Fluids. 2014; 58: 1848). This creates a divergence-free velocity field that only slightly adjusts the interpolated flow field but does not significantly affect it. Following the theory developed for the fractional step method in computational fluid dynamics, the interpolated velocity field is projected into a divergence-free subspace. This projection is carried out by an appropriate pressure distribution to correct the velocity field. In fact, it is the gradient of the pressure distribution in the Navier-Stokes equations, which significantly affects the velocity field's divergence. The final corrected velocity field satisfies the flow's incompressibility and continuity conditions. We have successfully tested this approach to reconstructing the LV and RV's 3D velocity and vorticity fields. This method is fully described (Falahatpisheh A et al. Exp Fluids. 2014; 58: 1848).

Figure 10:
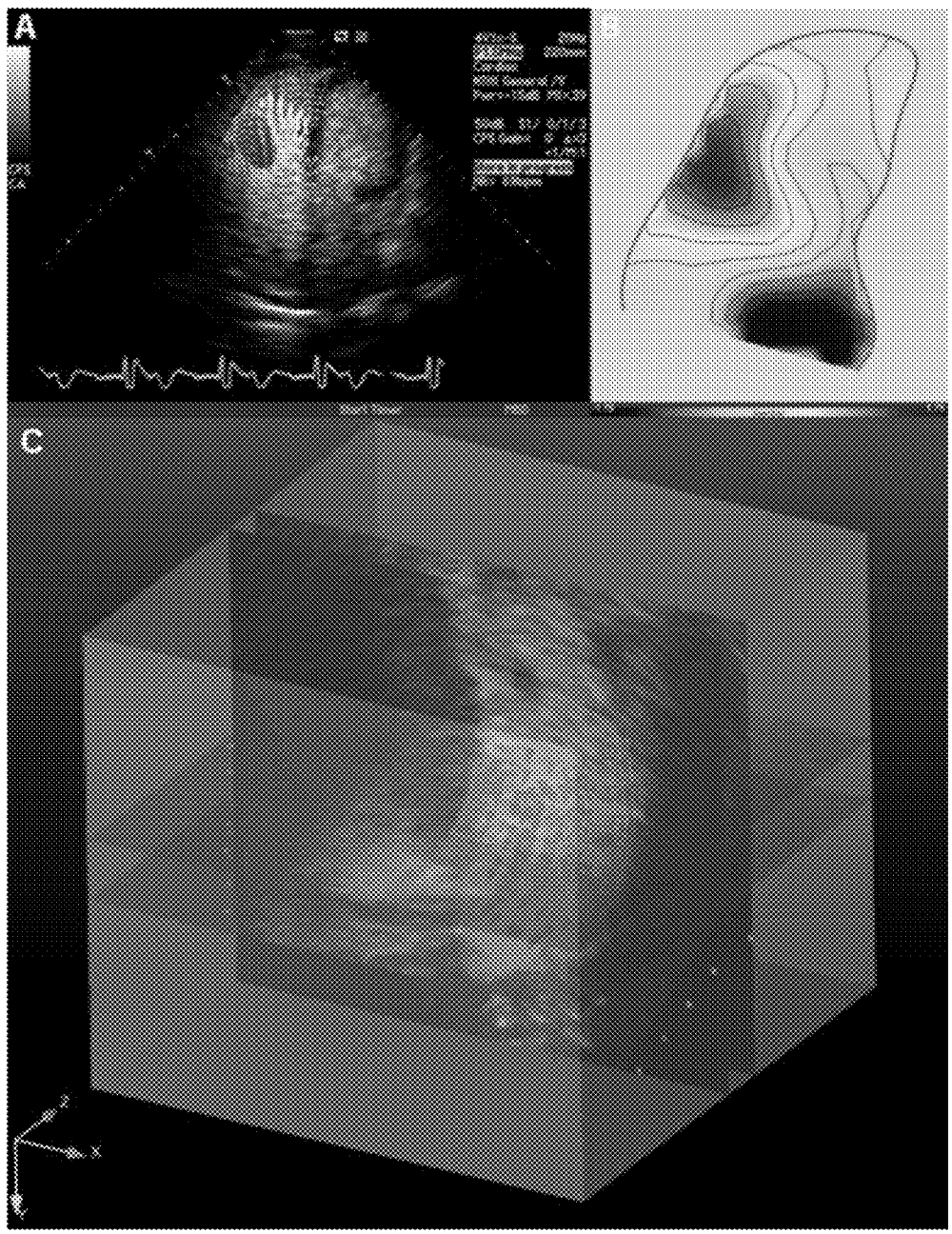
FIG. 10: (A) RV Velocity field at the peak diastole in a patient with systolic dysfunction with RV volume overload obtained from 2D Echo-PIV; (B) Circulation ($cm^2/s$) map of trans-tricuspid vortex from the same patient. Inset map defines the direction of rotation (dark gray/black is clockwise rotation, and light gray is counter-clockwise rotation). (C) 3D Echo PIV of a normal right ventricle showing the early diastolic trans-tricuspid flow.

For Echo-PIV purposes, since the RV is viewed from a sector perspective and the data are stored in cylindrical coordinates, they are converted to rectangular Cartesian coordinates using transformations $x=r \cos \theta$ and $y=r \sin \theta$, where x and y are the Cartesian coordinates, r is the radius, and $\theta$ is the phase of each point in a 2D echo-PIV plane. Then a predefined mask filters out the stationary parts of the images and detects the RV's moving boundary via image processing techniques. An ordered 3D Cartesian mesh was generated whose velocity field is obtained by Kriging 4D interpolation of a time-varying, 3D velocity vector field (Li L et al. Computers, Environment and Urban Systems. 2004; 28:201-227; Donald E M. Geoderma. 1994; 62:17-28). Kriging is a group of geostatistical techniques to interpolate the value of a random field at an unobserved location from observations of its value at nearby locations. FIG. 10C shows the early diastolic RV flow in a normal heart obtained using our developed multiplanar 3D Echo-PIV. FIGS. 10A and 10B show the RV velocity field at the peak diastole in a patient with systolic dysfunction with RV volume overload along with the circulation map of trans-tricuspid vortex. This method works at all the conventional frame rates and can compensate for situations where frame rates of 3D echocardiography are too low for direct volumetric acquisitions.

Direct Volumetric Echo-PIV

Figure 13:
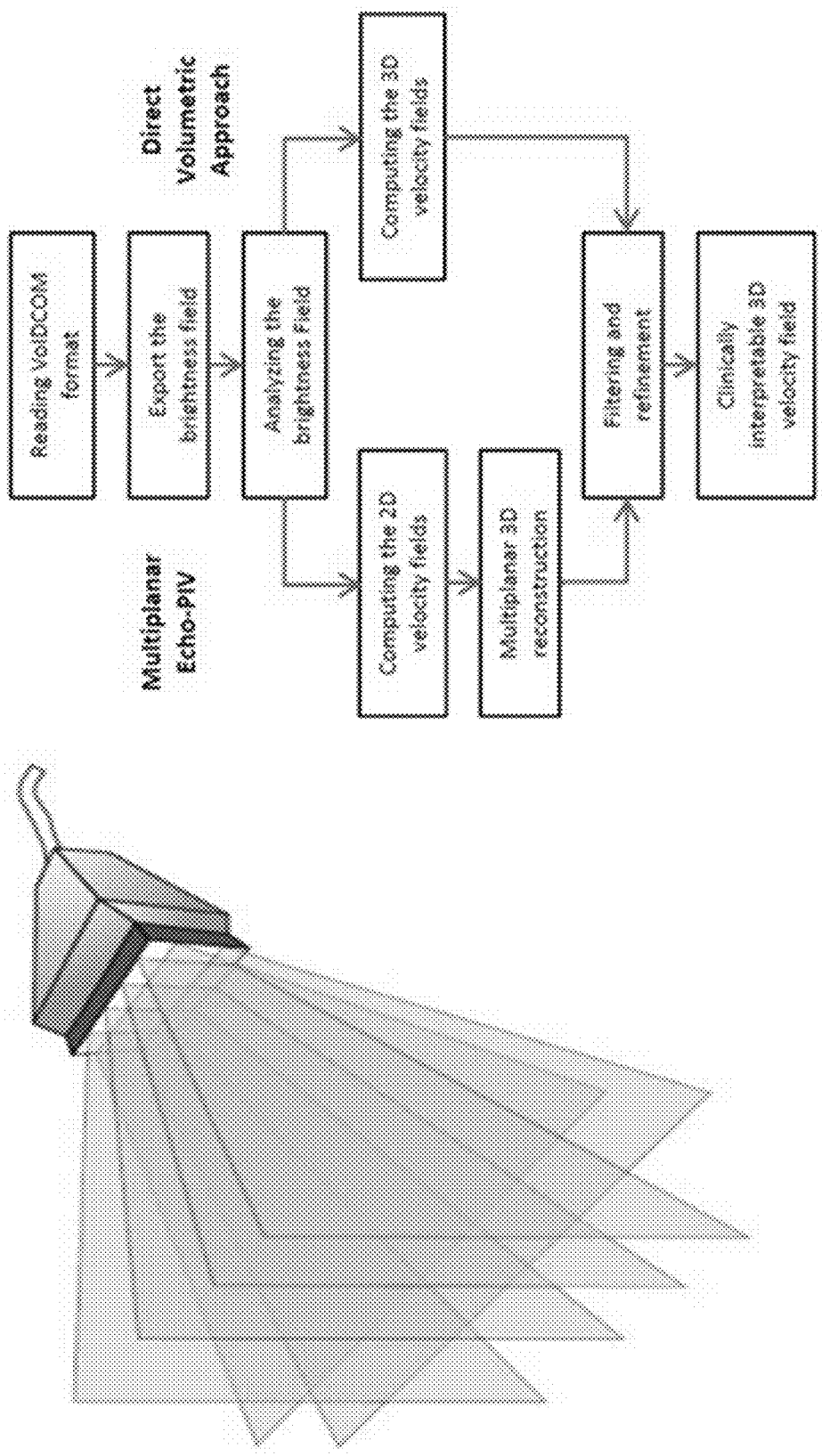
FIG. 13: (Right) A diagram showing how different approaches of 3D EchoPIV work. The acquisition process is similar. However, multiplanar reconstruction uses fewer ultrasound beams instead of all the beams. This enables the transducer (Left) to complete scanning faster during a single heartbeat. These probes are currently used to perform 3D echocardiography of heart chambers. The left panel shows a schematic of the multiple planes. For volumetric PIV all the beams are activated, guaranteeing better spatial resolution at a cost of lower temporal resolution.

Another approach for 3D Echo-PIV is a direct volumetric approach that complements the multiplanar flow reconstruction. Using this method, the transport equation for the brightness field, $B(x, y, z, t)$:

$$\frac{\partial}{\partial t}B + v_x \frac{\partial}{\partial x}B + v_y \frac{\partial}{\partial y}B + v_z \frac{\partial}{\partial z}B = 0 \qquad (7)$$

is directly solved in three dimensions and the 3D velocity field is acquired without the need to reconstruct the 2D fields. This method starts with acquiring volumetric images using matrix array probes, as schematically shown in FIG. 13, in which ultrasound contrast agent creates the required images for processing the contrast agent's motion (or even red blood cells (RBCs) with our recent progress; FIGS. 11A and 11B) in time. Each time-step compares two consecutive 3D images. The entire image is divided into small volumes (e.g., 16×16×16 voxels). The comparison is based on the conservation of brightness in each volume element at two consecutive times (time t1 and t1+dt). This conservation simply states that the bright voxels in the domain have a velocity equal to that of the blood flow. Considering this rule for every voxel in the volume element obtains a system of equations that can be solved by the least squares method. The solution to this system of equations is a velocity vector that is assigned to each processed volume element. This process continues until all the small volumes in the dataset are processed and assigned a velocity vector. This process obtains a 3D velocity field (FIGS. 11C and 11D) which are used to visualize blood flow features such as vortex flow and streamlines, and to characterize anomalies that may be present in the flow, such as, but not limited to abnormal shear stresses and Reynold stresses. Compared to the multiplanar version, this method's advantage is the simplicity of its computations, which can be more readily used for real-time applications. However, if the acquisition frequency is lower than 30 volumes per second for high spatial resolution data, this method cannot be used to accurately identify the velocity field. Nonetheless, in that case the multiplanar approach can still result in acceptable accuracy (Falahatpisheh A et al. Exp Fluids. 2014; 58: 1848). Therefore, our approach combines the two methods in our 3D Echo-PIV package to accommodate all acquisitions regardless of their spatial and temporal resolutions.

Using 3D Echo-PIV, we quantify the RV flow pattern in patients with RV systolic dysfunction, and compare them with the data from 4D Flow MR, and with results from the subjects with normal RV. RV strain and strain rate are analyzed for the same group of patients and normal subjects. Finally, we devise novel indices based on the RV flow and strain features for detecting and characterizing RV dysfunction.

We quantify the 3D flow field of the right ventricle in patients with RV systolic dysfunction due to pressure overload as a result of pulmonary hypertension, and compare them with 4D Flow MR. All results are compared with results of patients with normal RVs.

The flow field inside the right heart of patients with RV dysfunction are studied through the use of 3D Echo-PIV and compared with age- and gender-matched control subjects. Comparison with 4D Flow MR is used to validate the large-scale flow features. This quantitatively identifies pathologic flow features related to RV dysfunction due to pressure overload.

Imaging Protocol

Figure 11:
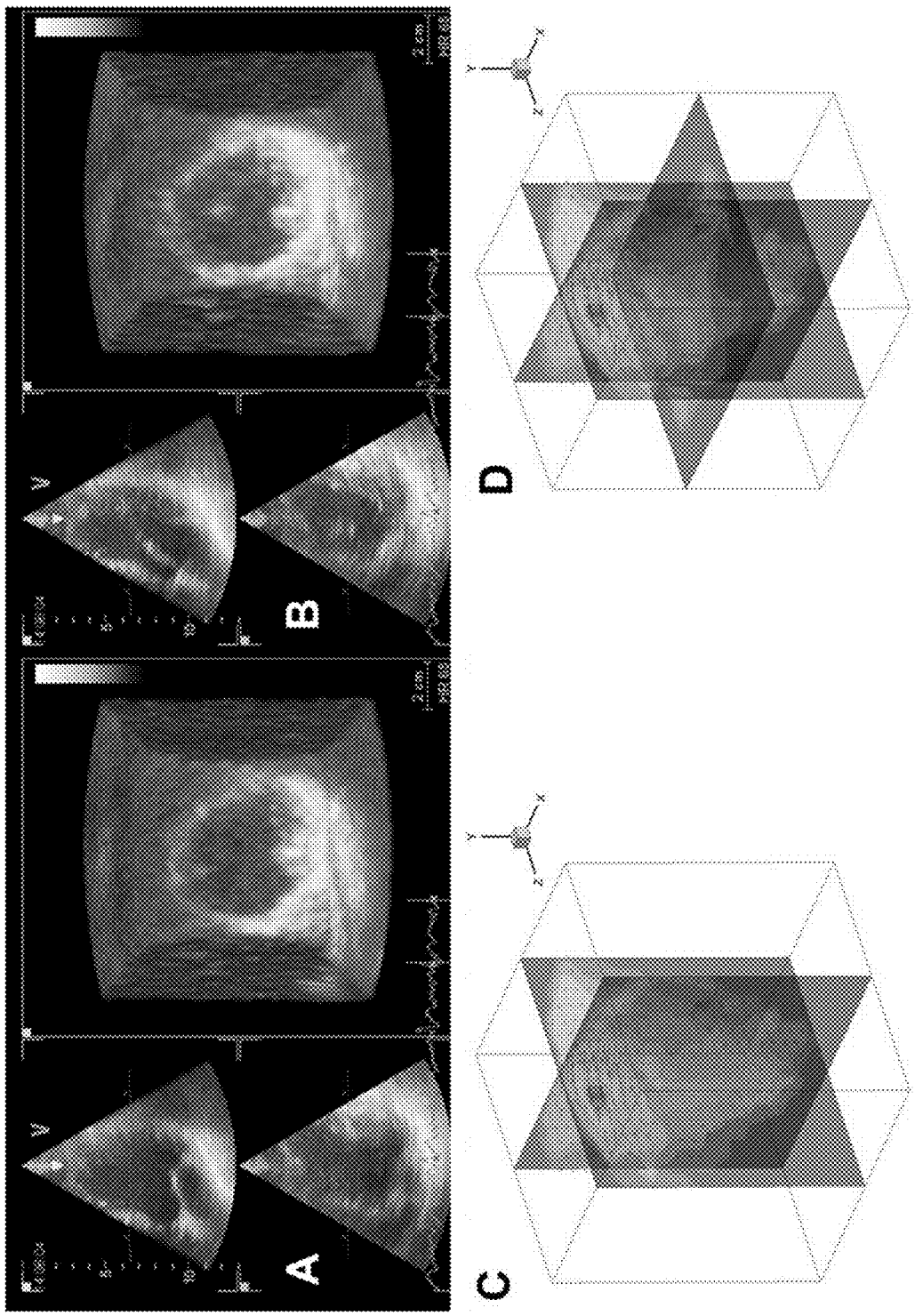
FIG. 11: Volumetric Echo-PIV with no contrast. (A) 3D echo without contrast showing the left heart during systole when the mitral valve is closed; (B) when the mitral valve is open; (C) instantaneous 3D velocity field of the LV when the mitral valve is open; transmitral jet is visible. Only two coronal and sagittal planes showed for ease of presentation. (D) the same 3D velocity field shown in (C) with addition of a short-axis plane for better presentation. (C) and (D) represent the same time point.
Figure 12:
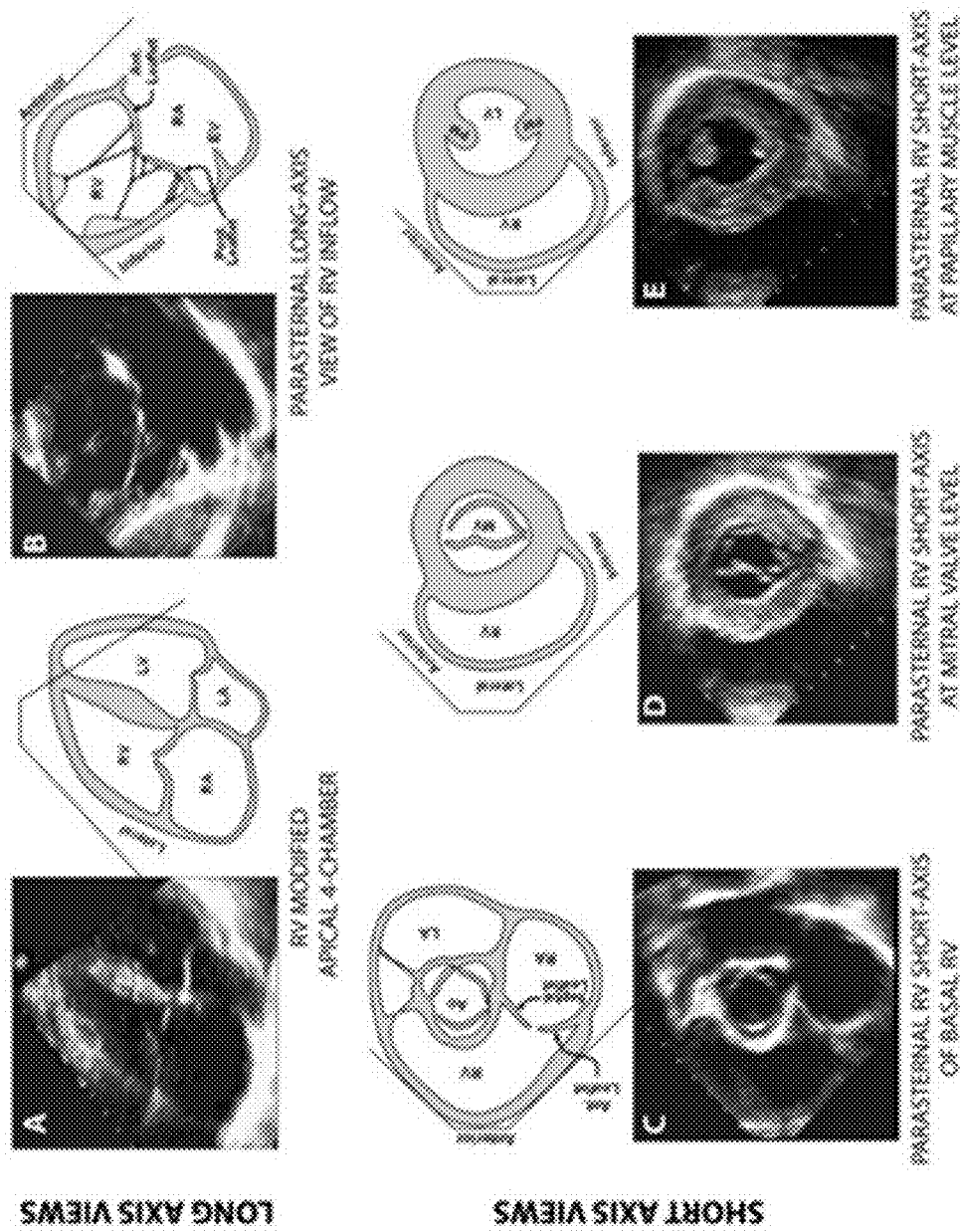
FIG. 12: Standard views used to perform 3D reconstruction of the RV flow field. (A) RV modified apical 4-chamber; (B) Parasternal long-axis view of RV inflow; (C) Parasternal RV short-axis of basal RV; (D) Parasternal RV short-axis at mitral valve level. (E) Parasternal RV short axis at papillary muscle level. The images are modified from the American Society of Echocardiography guidelines on RV function (Rudski L G et al. Journal of the American Society of Echocardiography 2010; 23:685-713).

A 3D matrix probe is used to acquire 3D acquisitions (either volumetric, as shown in FIG. 11, or multiplanar, which requires a simultaneous RV modified apical 4-chamber view and parasternal long-axis view of RV inflow (Rudski L G et al. Journal of the American Society of Echocardiography 2010; 23:685-713), followed by three individual transverse recordings of parasternal short axes at papillary muscle level, mitral level, and basal RV (Rudski L G et al. Journal of the American Society of Echocardiography 2010; 23:685-713), as shown in FIG. 12) for the RV flow field. The software decides on the type of 3D Echo-PIV based on the images' temporal and spatial resolution according to the algorithm in FIG. 13. Overall, the acquisition process is similar. However, multiplanar reconstruction uses fewer ultrasound beams instead of all the beams. This enables the transducer (FIG. 13 Left) to complete scanning faster during a single heartbeat. These probes are commercially available and currently used for performing 3D echocardiography of heart chambers. Volumetric PIV activates all the beams, guaranteeing better spatial resolution at the cost of lower temporal resolution. Our software chooses the best method for processing the data according to the spatial and temporal resolution of acquired images. Siemens Acuson™ c512 ultrasound systems are used for data acquisition. Blood flow visualization is enhanced by intravenous bolus administration of 0.1 to 0.2 ml standard contrast agents, diluted in 10 ml of saline solution. Results show the possibility of visualizing RV flow without contrast agent as shown in FIG. 11. This technique significantly facilitates routine clinical use, and the methods used verify its viability.

Figure 14:
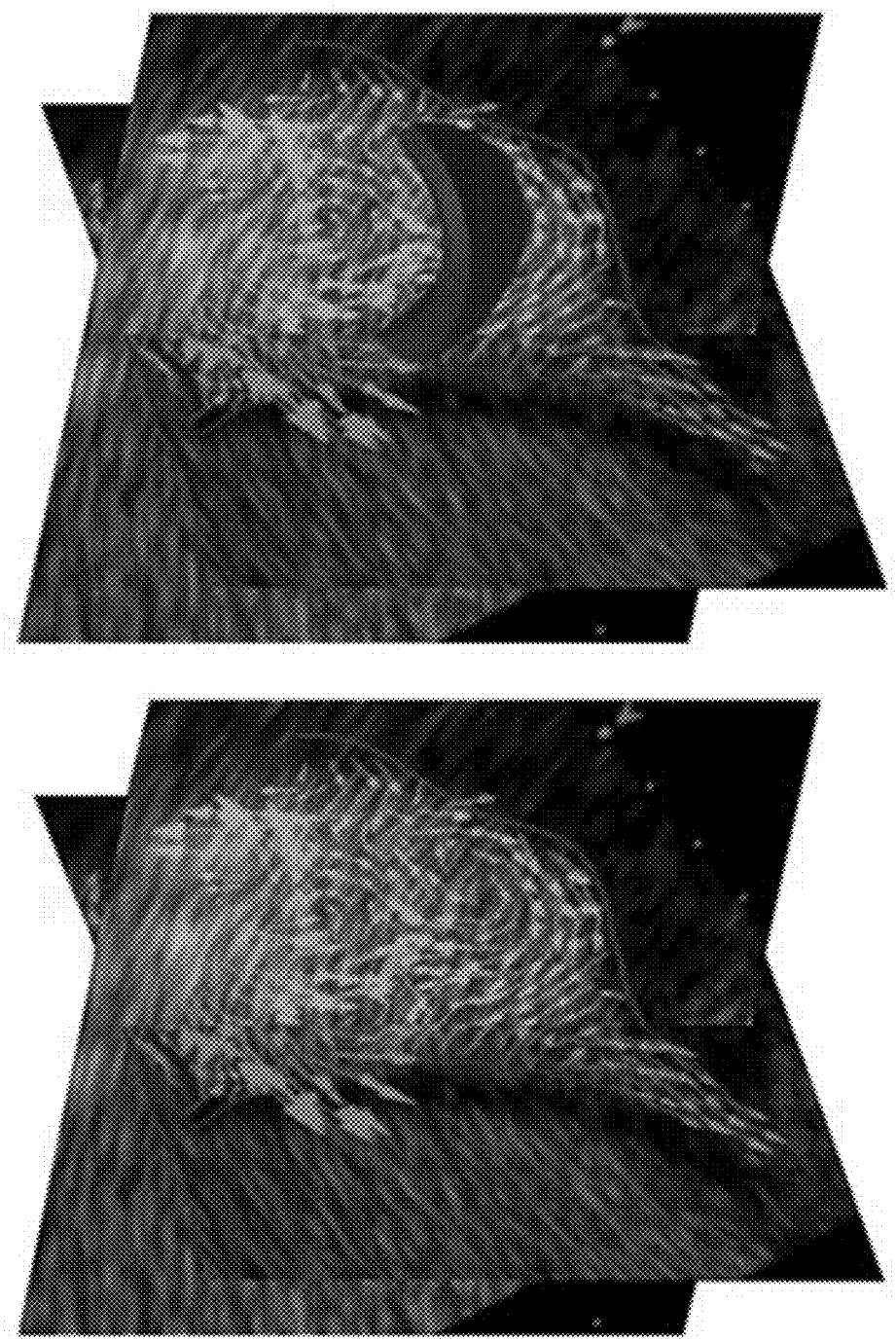
FIG. 14: Results from multiplanar 3D Echo-PIV, showing a vortex being formed from trans-tricuspid jet during diastole in a patient with RV dysfunction. 3D reconstructed vortex is shown in the right panel and is illustrated by iso-surfaces of $\lambda 2$ obtained from the velocity gradient tensor. A light gray line defines the RV boundaries obtained from RV modified apical 4-chamber view and parasternal long-axis view of RV inflow. The light gray vectors are in-plane velocities acquired by echo-PIV in two perpendicular planes intersecting the RV axis.
Figure 15:
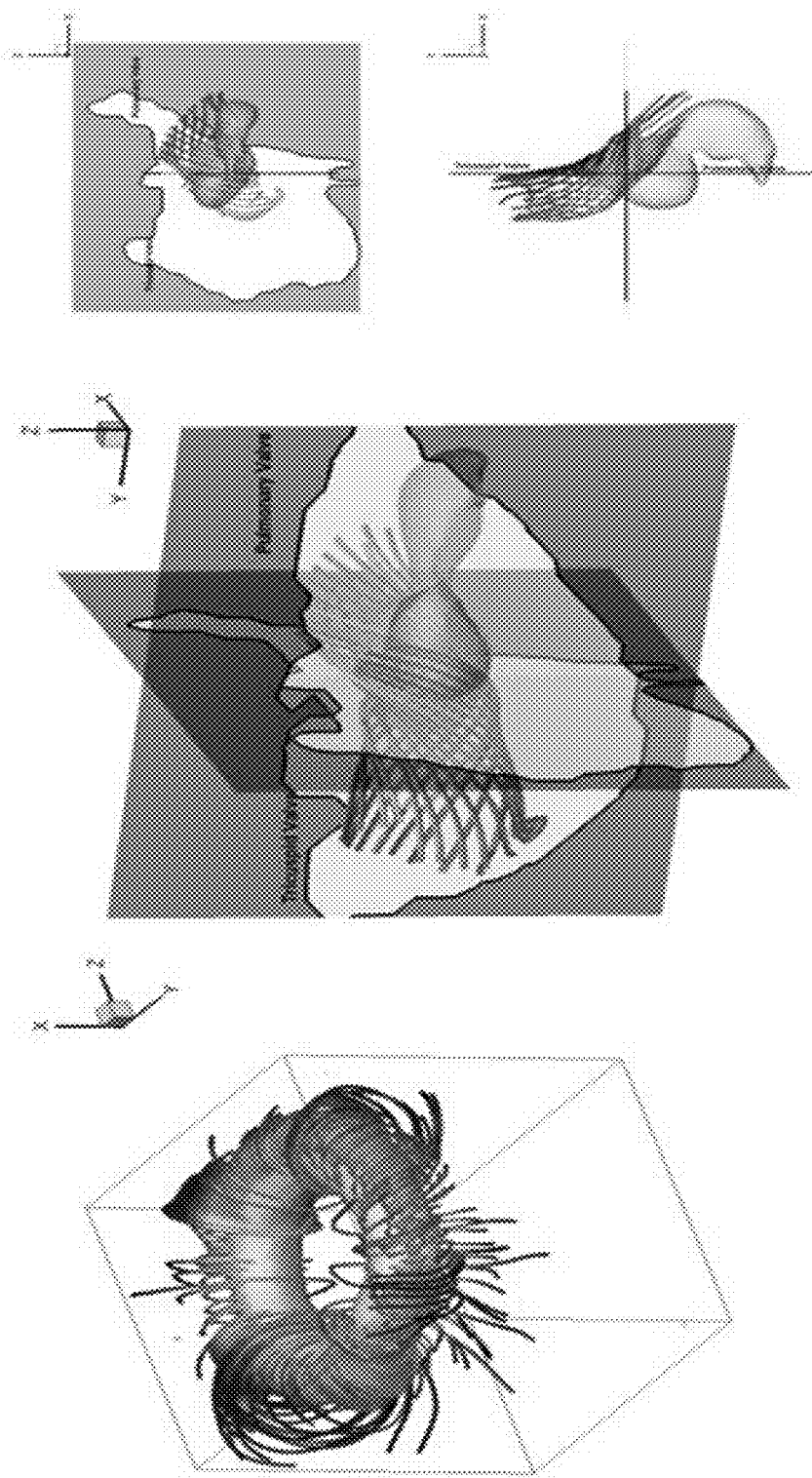
FIG. 15: (Left) the vortex core identified along with the streamlines; (Right) the RV vortex along with the streamlines translating from the tricuspid valve toward pulmonary outlet in the RV.
Figure 16:
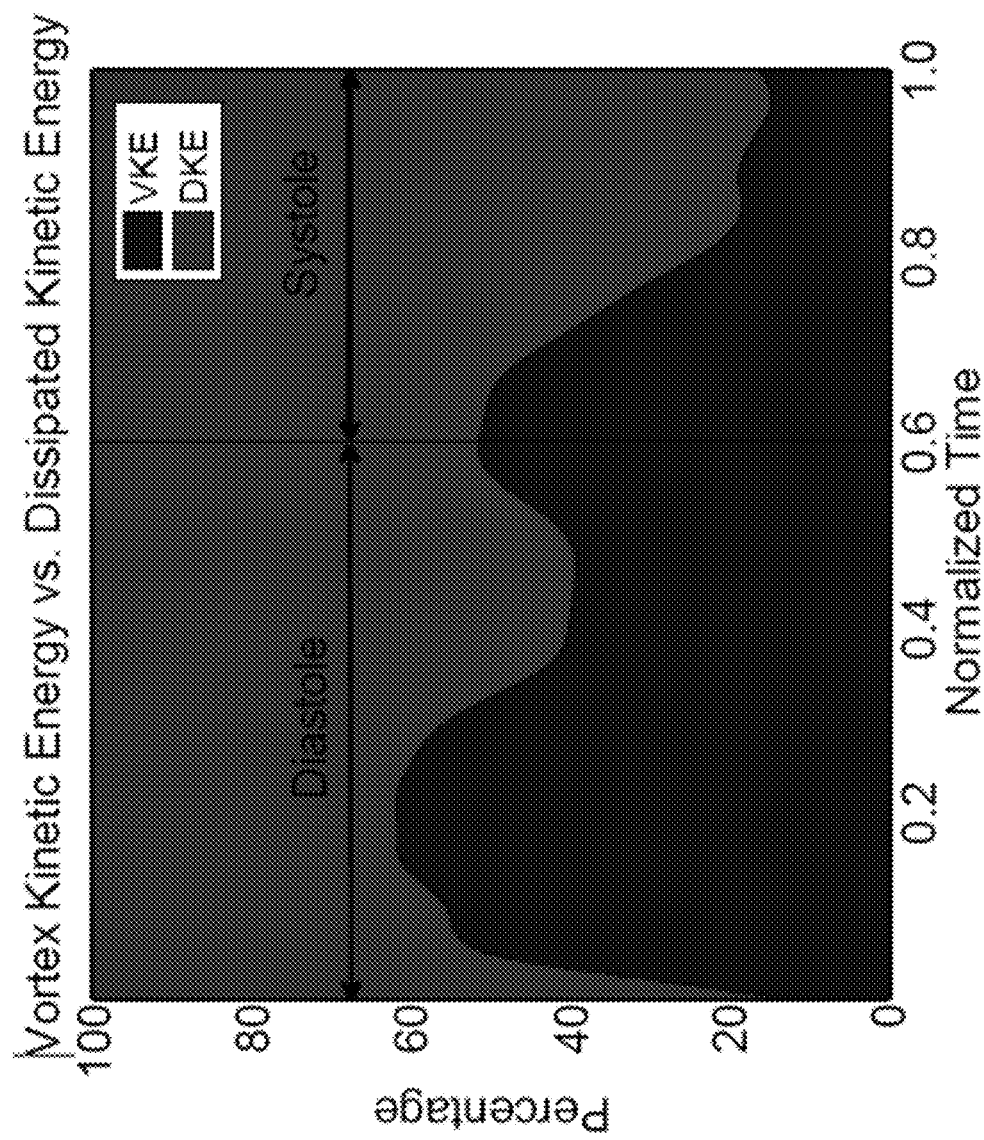
FIG. 16: Vortex kinetic energy (black) versus dissipated kinetic energy (gray) in one cycle in the RV. The onsets of diastole and systole are shown.

Obtaining RV Fluid Dynamics in 3D in Subjects with RV Dysfunction and Normal RVs The 3D Echo-PIV technique is applied to understanding RV fluid dynamics in subjects with normal RV and in patients with RV dysfunction (FIG. 14). During diastole, the normal 3D RV flow structure is expected to develop, an irregular ring-shaped vortex forming from the shear layer that emerges from the tricuspid valve leaflets (FIGS. 15 and 16). During the formation process, the vortex propagates away from the tricuspid valve's leaflets and entrains the ambient fluid inside the RV until it is pinched off from the trans-tricuspid jet. The helically toroidal-shape of the RV vortex (FIG. 15) is alleged to be due to the RV's crescent shape. This vortex has partly uneven nearby boundaries and eventually forms longitudinal vortices (i.e., circulations visible on the transversal planes, similar to FIG. 15). This process visualizes RV vortex formation through the tricuspid valve, as well the spiraling outflow during early systole. For the first time, this project visualizes and quantitatively evaluates such fundamental elements of RV fluid dynamics by echocardiography. The same technique is employed to evaluate the RV flow field in patients with RV dysfunction. The results allow the RV flow field to be quantitatively assessed in the presence of systolic RV dysfunction, and help to distinguish between abnormal and normal flow fields.

It is more challenging to determine RV than LV systolic function, and compared with the LV, the base-to-apex shortening has a more significant role in RV emptying (Rudski L G et al. Journal of the American Society of Echocardiography 2010; 23:685-713). Currently, there is a lack of outcomes data relating to quantifying RV systolic function by strain analyses. However, strain analyses, and particularly strain rate, have been strongly correlated with myocardial contractility (Jamal F et al. Am J Physiol Heart Circ Physiol. 2003; 285(6):H2842-7). We measure 3D strain and strain rates in our study subjects. Our novel index, the systolic RV strain index, is calculated for each patient and control subject. The index's sensitivity and specificity for diagnosing RV systolic dysfunction are quantified according to current available guidelines (Rudski L G et al. Journal of the American Society of Echocardiography 2010; 23:685-713). Furthermore, the obtained results are compared with the information related to 3D flow features inside the RV. Association between abnormal RV flow features and the systolic RV strain index is investigated.

A lower than normal index along with abnormal flow is expected to show signs of RV dysfunction. We devise novel diagnostic indices to detect and characterize RV dysfunction based on the acquired 3D flow fields, RV strain and RV strain rate.

Echocardiographic-based vortex imaging is extended to the right heart to test whether RV flow features such as vortex formation can be correlated to RV strain and strain rate in RV dysfunction and whether it is possible to define diagnostic measures for early-stage dysfunction according to the data from RV flow and RV strain analyses.

We develop quantitative diagnostic measures for the 3D intraventricular flow in RV, the trans-tricuspid vortex is automatically delineated by a thresholding procedure on the scalar quantity most appropriate for vortex detection (typically the $\lambda 2$ method is employed (Jeong J et al. J. Fluid Mech. 1995; 285:69-94), but other methods such as vorticity contour can also be used). This allows the vortex and flow properties to be quantified by well-established fluid dynamics analysis techniques (FIGS. 14 and 15). Vortex is characterized by its circulation on specific physiological planes (FIG. 15), on which we identify quantities that describe the vortex's geometry, pulsatility, and formation characteristics during the cardiac cycle. Vortex geometry is characterized by its relative position inside the ventricle, and its depth, length, width, and sphericity. The Vortex Sphericity Index (SI) (Kheradvar A et al. J Am Soc Echocardiogr. 2010; 23:3102-3111; Hong G R et al. JACC Cardiovasc Imaging. 2008; 1:705-717) given by the vortex's width-to-length ratio, provides a non-dimensional measure by which to characterize and compare the vortex's shape. Vortex Pulsatility Coefficient (VPC) (Sun Md J P et al. The American Journal of Cardiology. 1997; 80:1583-1587) is a dimensionless measure of vortex unsteadiness and is obtained through time-Fourier decomposition of the vorticity distribution and a comparison of the strength of the fundamental Fourier harmonic (average vorticity distribution) with that of the first harmonic (pulsatility component of vorticity distribution) at the same vortex position. Comparison is made by the ratio of pulsatile component to the average component (relative pulsatile strength), and by measuring the cross-correlation between the two (pulsatility correlation index). Another index that has been informative for grading diastolic dysfunction in the left heart is Vortex Formation Time (VFT) (Kheradvar A et al. Journal of the American Society of Echocardiography 2012; 25:220-227, Belohlavek M. European Heart Journal—Cardiovascular Imaging. 2012; Gharib M et al. Proc Natl Acad Sci USA. 2006; 103:6305-6308; and Kheradvar A et al. Annals of biomedical engineering. 2007; 35:2050-2064). VFT, a non-dimensional measure of transmitral vortex formation (Kheradvar A et al. Journal of the American Society of Echocardiography 2012; 25:220-227; Kheradvar A et al. ASAIO J. 2007; 53:8-16; Gharib M et al. Proc Natl Acad Sci USA. 2006; 103:6305-6308; Kheradvar A et al. Annals of Biomedical Engineering. 2009; 37:1-13; and Kheradvar A and Pedrizzetti G. Vortex formation in cardiovascular system. Springer; 2012) is computed as the ratio of a starting jet's length to diameter (Gharib M et al. J Fluid Mech. 1998; 360:121-140). VFT has been shown to provide additional information on grading abnormal filling patterns and diastolic dysfunction (Kheradvar A et al. Journal of the American Society of Echocardiography 2012; 25:220-227). VFT is tested for the trans-tricuspid jet. We statistically test whether any of these indices in RV, computed for trans-tricuspid flow, change significantly in subjects with RV dysfunction, and if a change is expected, whether it correlates with the dysfunction grade/type.

Correlation with RV Wall Thickness

We measure the RV wall thickness in subjects with RV systolic dysfunction and in the control subjects. Then, we test whether any correlation exists between the wall thickness and flow-related indices. If a statistically significant correlation is found, we stratify our analysis by the presence or absence of RV hypertrophy (RV free wall thickness greater than 5 mm in the subcostal view).

Computation of Kinetic Energy

In an ideal situation, the kinetic energy of the trans-tricuspid flow is transferred to the pulmonary trunk via the RV with minimal loss. Optimal formation of the trans-tricuspid vortex helps effective transfer of the blood flow's circulation, impulse, volume, and energy, and requires a vigorous RV to generate adequate suction, properly-sized tricuspid/pulmonary valves that direct the blood jet through, and a normal electrical conduction system that allows ventricular events in harmony (Narula J et al. Journal of the American College of Cardiology. 2007; 49:917-920). In a normal heart, the main RV vortex assists effective energy transfer and minimize the stroke work. However, formation of abnormal vortices can drastically dissipate the flow's kinetic energy through the right heart. It is expected that changes in RV structure and function in the presence of RV dysfunction permanently affects RV vortex formation and energy. In these patients, most of the kinetic energy should be dissipated due to the formation of small vortices (non-coherent background flow field), which are disconnected from the main vortex (coherent flow structure). Here we compute the kinetic energy of the flow field in systolic RV dysfunction and compare the result to that of normal RV in control age- and gender-matched subjects.

Computation of RV Energy Dissipation

To obtain the dissipation of kinetic energy (DKE, the kinetic energy related to the non-coherent structures through computational fluid dynamics), vortex kinetic energy (VKE, the kinetic energy related to coherent structures) is subtracted from the chamber's total kinetic energy (TKE) during the cycle. Total kinetic energy of RV flow and the vortex kinetic energy are computed as:

$$TKE = \int_{RV} \tfrac{1}{2}\rho\|u\|^2 dV \text{(3) and } VKE = \int_{Vortex} \tfrac{1}{2}\rho\|u\|^2 dV \qquad (8)$$

respectively; where $\rho$ is the fluid density, $\|u\|$ is the velocity magnitude, and dV is the volume element. As mentioned earlier, we consider "dissipation" as the amount of kinetic energy devoted to non-coherent flow structures versus coherent structures such as the vortex ring. The dissipation is computed as the difference between TKE and VKE. Since the 3D velocity field is obtained using 3D Echo-PIV and 4D Flow MR, the above equation changes to:

$$VKE = \Sigma_{Vortex} \tfrac{1}{2}\rho\|u\|^2 \Delta V = \Sigma_{i=1}^{N} \tfrac{1}{2}\rho\|u\|^2 \Delta V_i \qquad (9)$$

where the summation is over all the nodes in the vortex regions in 3D space (FIG. 15), and N is the total number of nodes that lie in that region. The next step is to identify the areas where a vortex (coherent structure) is present. We use the Lambda-2 ($\lambda$2) method (Jeong J et al. J. Fluid Mech. 1995; 285:69-94), a reliable technique for identifying vortex regions in complex and three-dimensional flow conditions. Lambda-2 ($\lambda$2) is the second eigenvalue of the 2nd order tensor S2+$\Omega$2; where S and $\Omega$ are the symmetric and skew symmetric parts of the velocity deformation gradient tensor, respectively. The $\lambda$2 method is used to identify vortex regions: regions where this eigenvalue is less than zero. The volume bounded by the triangulated surface of the $\lambda$2 constant is discretized into finite volumes. VKE is the summation of $\rho\|u\|^2\Delta V/2$ for all those volume elements. Similarly, TKE of the RV will be computed through finite volumes. The graph in FIG. 16 shows the variation of vortex and dissipated kinetic energy in a cardiac cycle with respect to the total kinetic energy in a normal RV model.

The SI, VPC, and VFT indices are non-dimensional parameters, and are expected to be load-independent, similar to those of the LV (Hong G-R et al. JACC: Cardiovascular Imaging. 2008; 1:705-717; Kheradvar A et al. Journal of American Society of Echocardiography. 2010; 23:86-94; and Kheradvar A et al. Journal of the American Society of Echocardiography 2012; 25:220-227). While no reported value currently exists for SI, VPC, and VFT, the ranges of these indices for a normal LV are reported as VPC between 0.18 to 1.31, SI between 2.00 to 3.66, and VFT between 3 and 5.5 (Hong G-R et al. JACC: Cardiovascular Imaging. 2008; 1:705-717; Kheradvar A et al. Journal of the American Society of Echocardiography 2012; 25:220-227; Kheradvar A et al. Journal of the American College of Cardiology. 2008; 51:A104; Gharib M et al. Proc Natl Acad Sci USA. 2006; 103:6305-6308; Kim D-H et al. Echocardiography. 2013; 30:588-598; Chan B T et al. PloS one. 2013; 8:e67097; Lampropoulos K et al. Cardiovascular Ultrasound. 2012; 10:5; Nucifora G et al. The American Journal of Cardiology. 2010; 106:1404-1409; Jiamsripong P et al. Journal of the American Society of Echocardiography. 2009; 22:427-431 and Goliasch G et al. JACC: Cardiovascular Imaging. 2013; 6:704-713). We compute TKE, VKE, and the dissipation due to abnormal vortices in both RV dysfunction and normal RV groups. We observe a correlation among RV wall thickness, systolic RV strain index, and the flow-related indices. It is anticipated that transtricuspid VKE in patients with RV dysfunction is significantly lower than that of normal RVs. This may represent excessive kinetic energy being dissipated as non-coherent flow structures increase the work load and decrease the right heart's pumping efficiency. Low VKE is associated with low systolic RV strain index and denotes RV systolic dysfunction.

Identifying RV vortex core can be challenging due to the complexity of the RV geometry, which may lead to less robustness in automated computation of the kinetic energy. To overcome this problem, we perform calculations at different threshold levels ($\lambda$2 level) to identify the vortex. If required, we also improve our vortex computational techniques, including the constraint of divergence-free to the vorticity field, similar to what previously has been done for the velocity vector field. This ensures a more coherent vorticity field, and adds small-scale filtering for vortex identification as the only coherent structure.

Example 3

A Framework for Synthetic Validation of Volumetric Particle Imaging Velocimetry

We provide a novel framework for validation of volumetric velocimetry methods with an emphasis on one based on 3D echocardiography. The presented framework creates 3D synthetic fields according to a known 3D velocity field V(x) and a given 3D brightness field B(x). The method begins with computing the inverse flow V*(x) based on the velocity field V(x). Subsequently the transformation of B(x), imposed by V(x), is calculated using the computed inverse flow according to B*(x)=B(x+V*(x)) with a 3D weighted average interpolation, which provides high accuracy, low memory requirement, and low computational time. To check the validity of the framework, we generate pairs of 3D brightness fields by employing known velocity fields. B(x) and B*(x) are then processed by our in-house 3D particle image velocimetry technique for comparison purposes against the given velocity field.

Two physically interrelated known 3D particle fields with a known velocity field can be used to compare and validate various 3D velocimetry techniques. We describe a method to reconstruct a synthetic three dimensional particle field according to a known velocity vector field applied to an originally random particle (or brightness) field.

Figure 17:
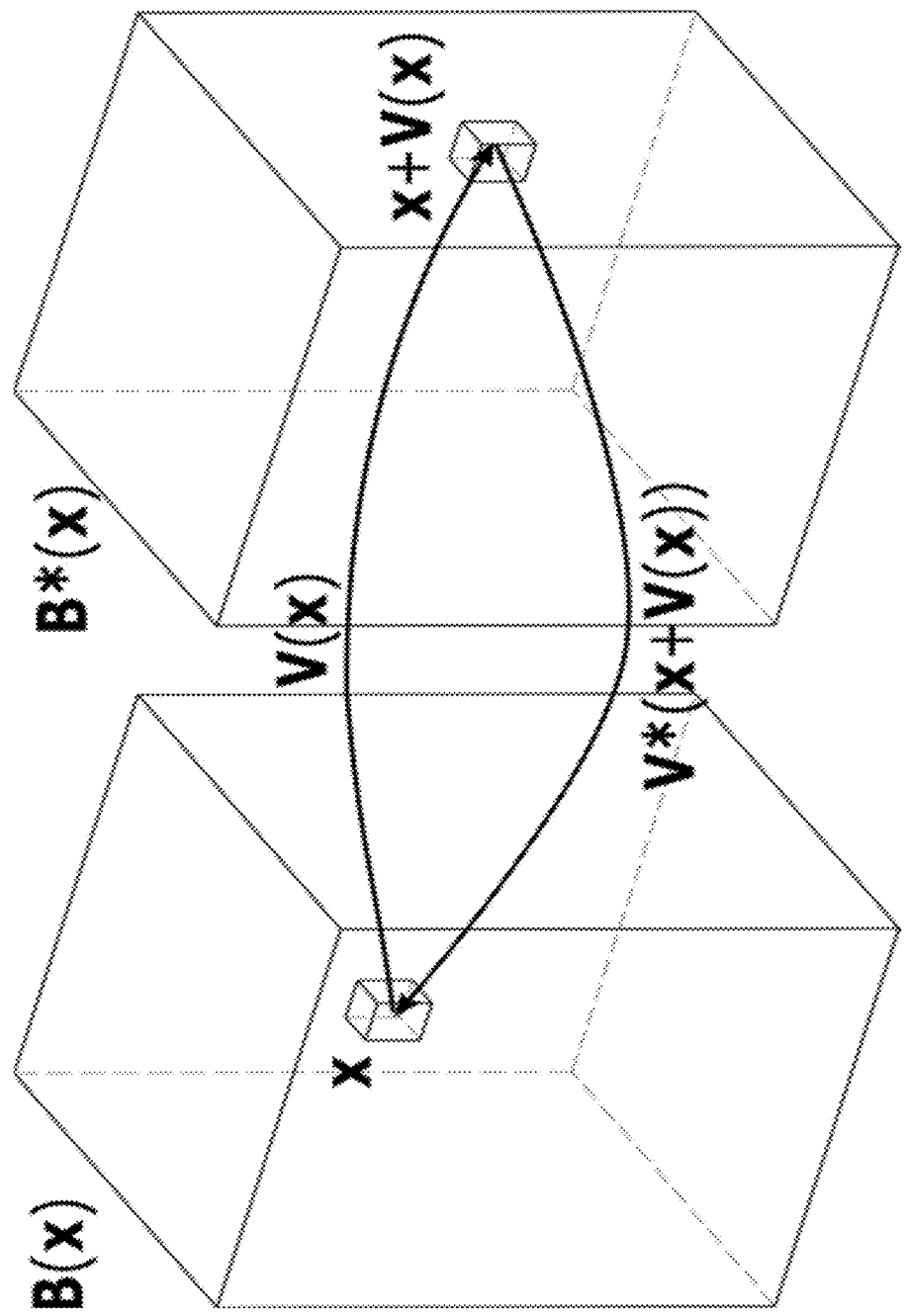
FIG. 17: Mapping of the voxel in the forward and inverse flows, $V(x)$ and $V^*(x)$, respectively.
Figure 18:
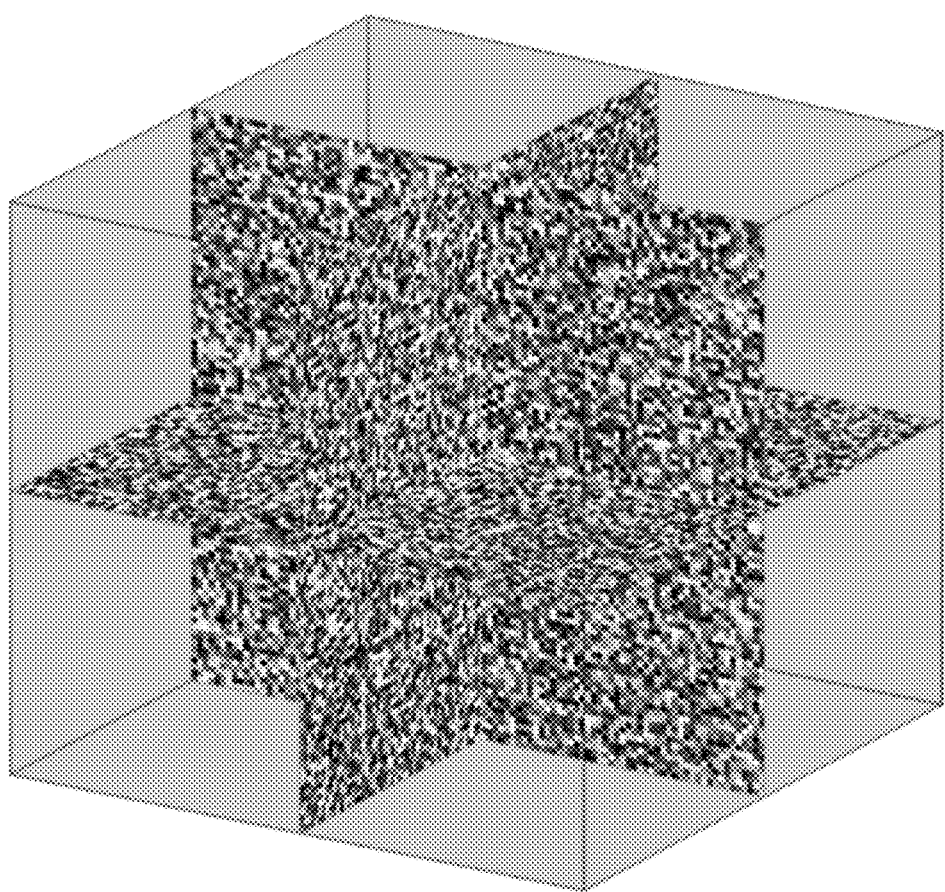
FIG. 18: Random brightness field, $B(x)$.

Generating synthetic three dimensional dataset for validation of volumetric particle image velocimetry starts with creation of two consecutive volumetric frames, B(x) and B*(x), where x=(x, y, z), and B and B* are grayscale three dimensional brightness fields. Our approach was to transform the first randomly-generated volumetric frame, B(x), using a known velocity field, V(x), to obtain the second volumetric frame, B*(x). In fact, V(x) establishes the relation between the voxels of the two frames, as shown in FIG. 17. Furthermore, V(x) is considered to be a dense mapping in such a way that for each voxel in B, there is a mapping for its corresponding voxel in B*. The process was initiated by populating a randomly-distributed, three dimensional grayscale brightness field into B(x), a structured array of size M×N×K, with random numbers in the range of 0 to 255, as illustrated in FIG. 18.

Suppose V(x)=(u(x), v(x), w(x)) is the forward flow, with u(x), v(x), w(x), as the horizontal, vertical, and depth displacements in each voxel x, respectively. The relation between the frames and the forward flow is defined as:

$$B(x)=B^*(x+V(x)) \tag{10}$$

Therefore, to compute B*(x), the value of each pixel B(x) should be copied to B*(x)=B(x+V(x)). However, since the value of V(x) is in float precision, the position x+V(x) does not coincide with the voxel grid. Here, we compute the inverse flow, V*(x), instead of the forward flow, and use the following relation to create the second frame, as shown in FIG. 17:

$$B^*(x)=B(x+V^*(x)) \tag{11}$$

Hence, the problem becomes the computation of the inverse optical flow:

$$V^*=\text{inv}(V) \tag{12}$$

We use an interpolation algorithm to find V*, as described by Sanchez et al. (Sánchez, J. Pattern Recognition Letters, 2015. 52(0): p. 32-39) and extend it to three dimensional data sets rather than 2D images. In fact, V*(x) maps the voxels in the second frame to the voxels in the first frame. Since the volumetric frames are discrete 3D datasets, correspondence of each voxel in the first frame may lie among several voxels in the second frame, instead of perfectly lying on the grid nodes, and therefore, a weighted average was used to address this:

$$V^*(x) = -\frac{\sum_{x_i \in N_i} \omega_i V(x_i)}{\sum_{x_i \in N_i} \omega_i} \qquad (13)$$

where $N_i \equiv \{x_i: \|x_i + V(x_i) - x\| < 1\}$, i.e., the set of correspondences that lie around x. The weights in the pseudocode above are illustrated in FIG. 19, where each weight represents the corresponding volume of the cell. Equation 13 was iteratively calculated to find the new value for a specific voxel. The algorithm was implemented in MATLAB (Math-Works, Natick, Mass.), as described in pseudocode 1 and 2.

---

Pseudocode 1 SelectMotion(d, V, wght, d*, V*, wght*)

```
if wght≥0.125 then
    if abs(d−d*)≤MOTION_TH then
        V* ← V*+V*wght
        wght* ← wght*+wght
    else if d ≥ d* then
        d* ← d
        V* ← V*wght
        wght* ← wght
    end
end
```

---

Pseudocode 2 Inverse Average Flow

```
Input: V
Output: V*
Initialize buffers d*, avg_V, wght* to 0
foreach position x do
    x_v ← x + V(x)
    Find the eight neighbors of x_v: {x_1, x_2, x_3, x_4, x_5, x_6, x_7, x_8}
    (see FIG. 19A)
    Compute the trilinear interpolation weights:
    w_1, w_2, w_3, w_4, w_5, w_6, w_7, w_8 (see FIG. 19B)
    d ← ‖V(x)‖²
    SelectMotion(d, V(x), w_1, d*(x_1), avg_V(x_1), wght*(x_1))
    SelectMotion(d, V(x), w_2, d*(x_2), avg_V(x_2), wght*(x_2))
    SelectMotion(d, V(x), w_3, d*(x_3), avg_V(x_3), wght*(x_3))
    SelectMotion(d, V(x), w_4, d*(x_4), avg_V(x_4), wght*(x_4))
    SelectMotion(d, V(x), w_5, d*(x_5), avg_V(x_5), wght*(x_5))
    SelectMotion(d, V(x), w_6, d*(x_6), avg_V(x_6), wght*(x_6))
    SelectMotion(d, V(x), w_7, d*(x_7), avg_V(x_7), wght*(x_7))
    SelectMotion(d, V(x), w_8, d*(x_8), avg_V(x_8), wght*(x_8))
end
foreach position x do
    V*(x) ← − avg_V(x) / wght*(x)
end
```

---

Generation of Interrelated Brightness Fields

We used the above-mentioned algorithm to create two brightness fields in three dimensions that represented the Hill's spherical vortex (HSV). This vortex is an extreme member of the Norbury family of vortex rings (Norbury, J. Journal of Fluid Mechanics, 1973. 57(03): p. 417-431), and is employed as a model in many applications such as the motion of droplets and bubbles at a high Reynolds number and for 3D PIV applications (Falahatpisheh, A. et al. Experiments in fluids, 2014. 55(11): p. 1-15). The vorticity inside the HSV is a linear function of the distance from the axis of symmetry. In a HSV, the internal flow has an axisymmetric vorticity distribution whereas the external flow is irrotational around a sphere.

A HSV is specified by the Stokes (axisymmetric) streamfunction as:

$$\psi = \begin{cases} \frac{3}{4} V_e r^2 \left(1 + \frac{\rho^2}{R^2}\right) \rho^2 \leq R^2 & \text{(internal flow)} \\ \frac{3}{4} V_e r^2 \left(\frac{R^3}{\rho^3} - 1\right) \rho^2 \geq R^2 & \text{(external flow)} \end{cases} \qquad (14)$$

where R specifies the size of the spherical vortex, $V_e$ is the external uniform vertical velocity; $r = \sqrt{x^2+y^2}$ and $\rho = \sqrt{r^2+z^2}$ are the cylindrical and spherical radial coordinates, respectively. The velocity field in Cartesian coordinates is computed by the streamfunction as:

$$u = \frac{x}{r^2}\frac{\partial \psi}{\partial z}; \; v = -\frac{x}{r^2}\frac{\partial \psi}{\partial z}; \; w = \frac{1}{r}\frac{\partial \psi}{\partial r} \qquad (15)$$

Transforming Velocity Field

We created a 3D velocity field, V(u(x), v(x), w(x)), with a resolution of 100×100×100 and unit radius and external velocity based on equations 14 and 15. This velocity field was used to transform B into B* based on the algorithm described earlier in the Methods section.

Validating an Exemplary Volumetric PIV Method

B and B* were accordingly processed by using an in-house Volumetric Echocardiographic Particle Image Velocimetry (V-Echo-PIV) software (Falahatpisheh, A. and A. Kheradvar Circulation, 2014. 130(Suppl 2): p. A14952). This software works based on iterative hierarchical PIV method to find the velocity vector fields. Our software was used here to examine whether it can obtain the velocity field corresponding to B and B*, and how close the resultant vector field is to the analytical HSV solution. Furthermore, we added Gaussian noise to the second frame, B*, to investigate how noise can adversely affect the velocity measurements. The level of noise was determined according to the signal-to-noise ratio (SNR). We considered 1, 2, 5, 10, 15, 25, 50, and 100 dB for SNR. The noise was incorporated during the processing of B and B*. We used three levels of hierarchy, i.e., coarsening and refining, as well as three-level iteration for each SNR in finding the velocity. The root mean square (RMS) error, reported here as a function of the signal to noise ratio, level of hierarchy, and number of iterations, statistically represents the difference between the analytical HSV and the computed velocity field using B and B*:

$$Err_{RMS} = \frac{\sqrt{\frac{1}{n}\sum [(u_{HSV}-u_{comp})^2 + (v_{HSV}-v_{comp})^2 + (w_{HSV}-w_{comp})^2]}}{V_{scale}} \qquad (16)$$

where n is the resolution of the three dimensional domain, subscript HSV refers to the analytical HSV and subscript Comp represents the computed velocity component and $V_{scale}$ is unity for the created HSV.

Figure 20:
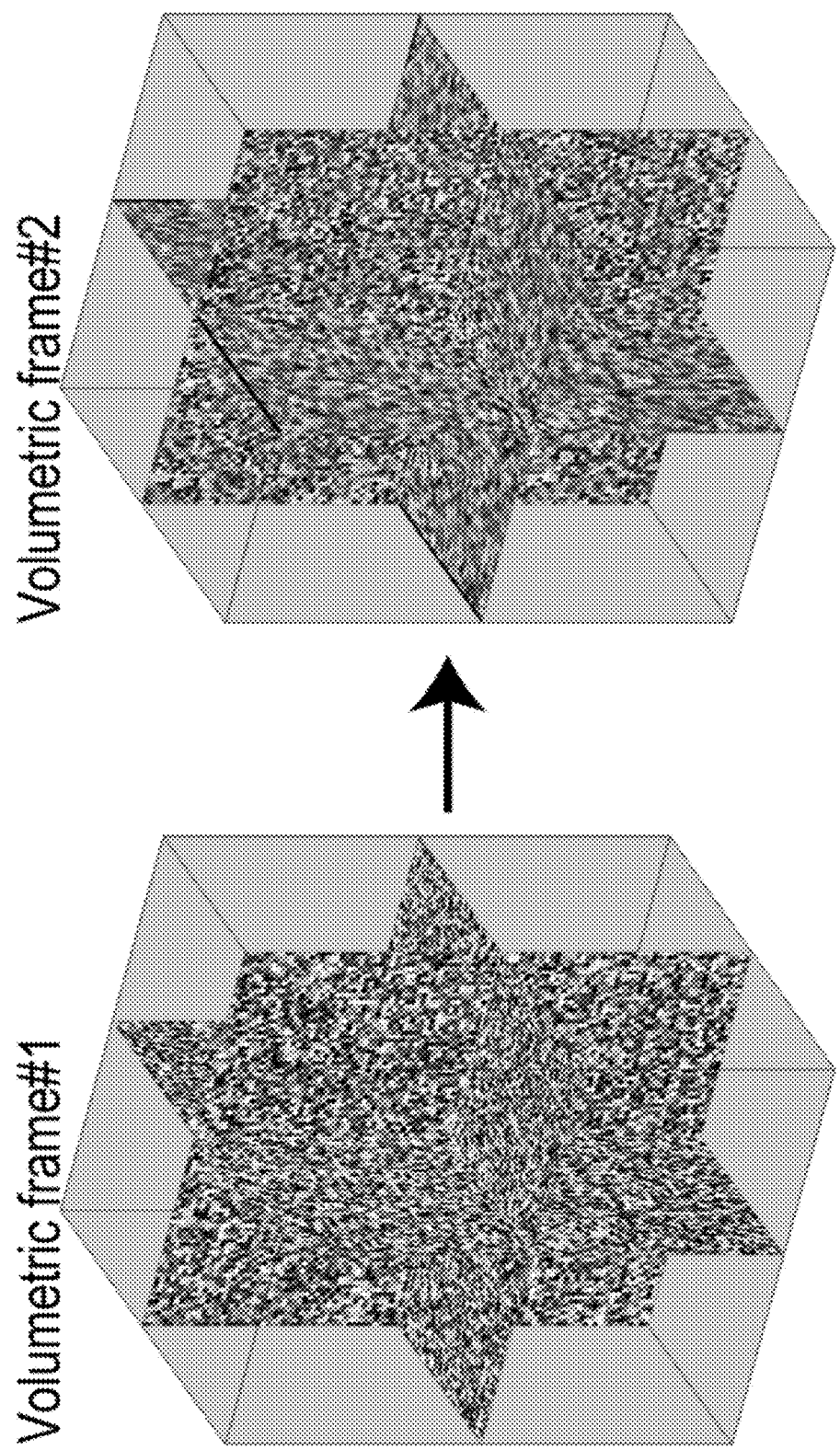
FIG. 20: Synthetic brightness field (Volumetric frame#2) generated using the random brightness field (Volumetric frame#1) in FIG. 18.
Figure 21:
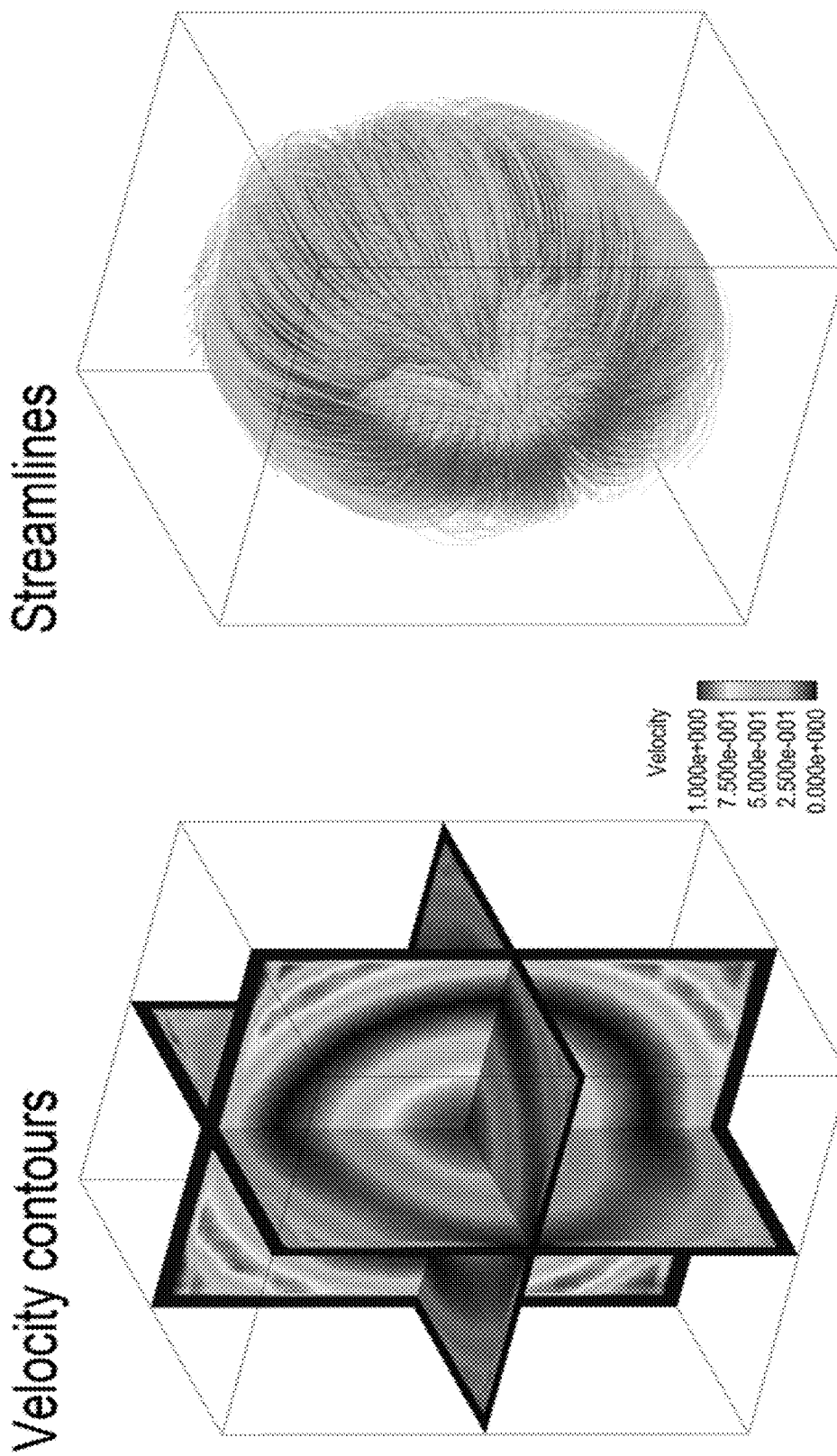
FIG. 21: Velocity contours and streamlines of Hill's spherical vortex obtained by V-Echo-PIV using the datasets in FIG. 20.
Figure 22:
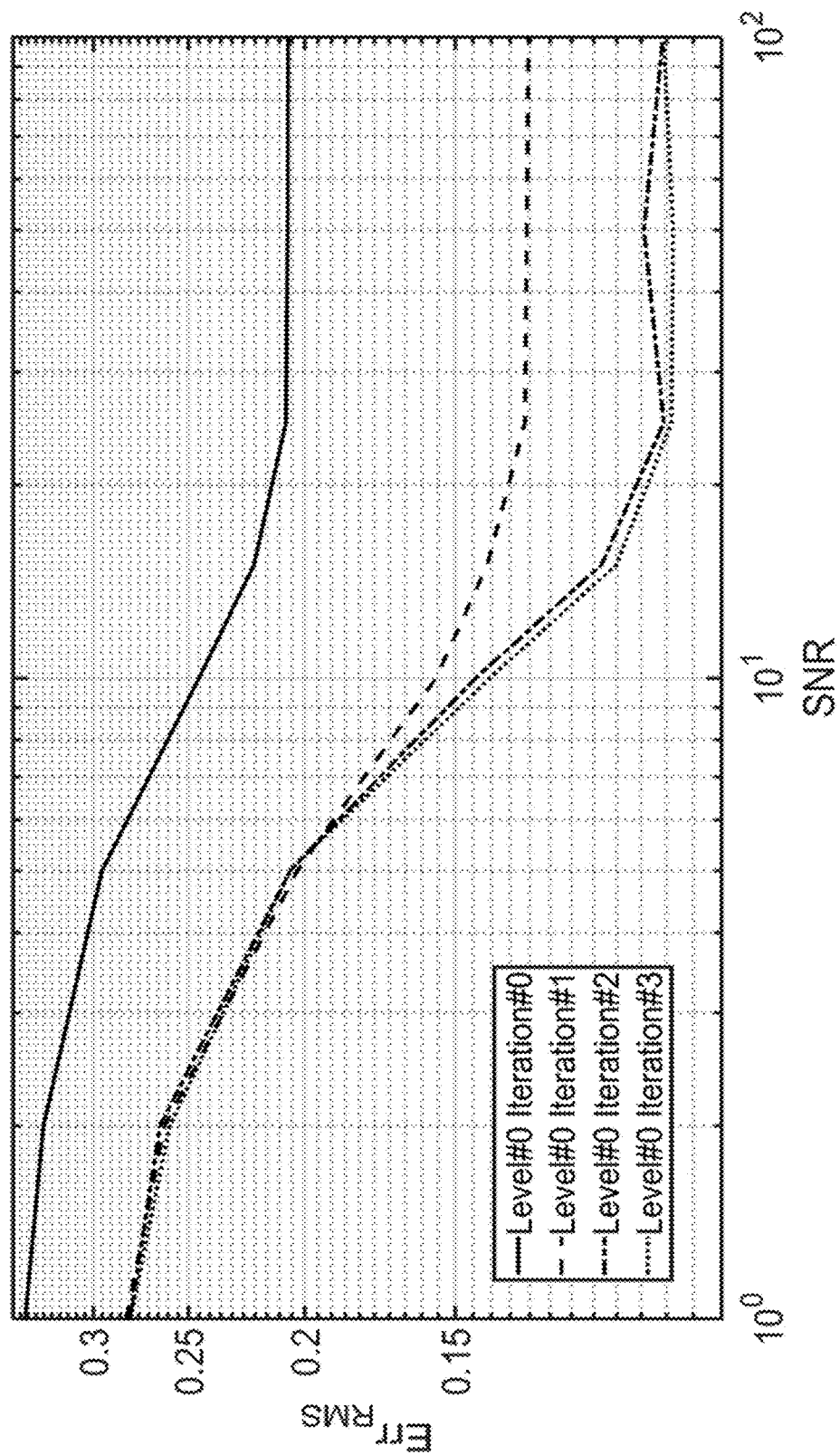
FIG. 22: The effect of number of iterations, i.e., number of times velocity was corrected, when no hierarchical PIV was implemented in V-Echo-PIV. Convergency was attained when the velocity was corrected three times.
Figure 23:
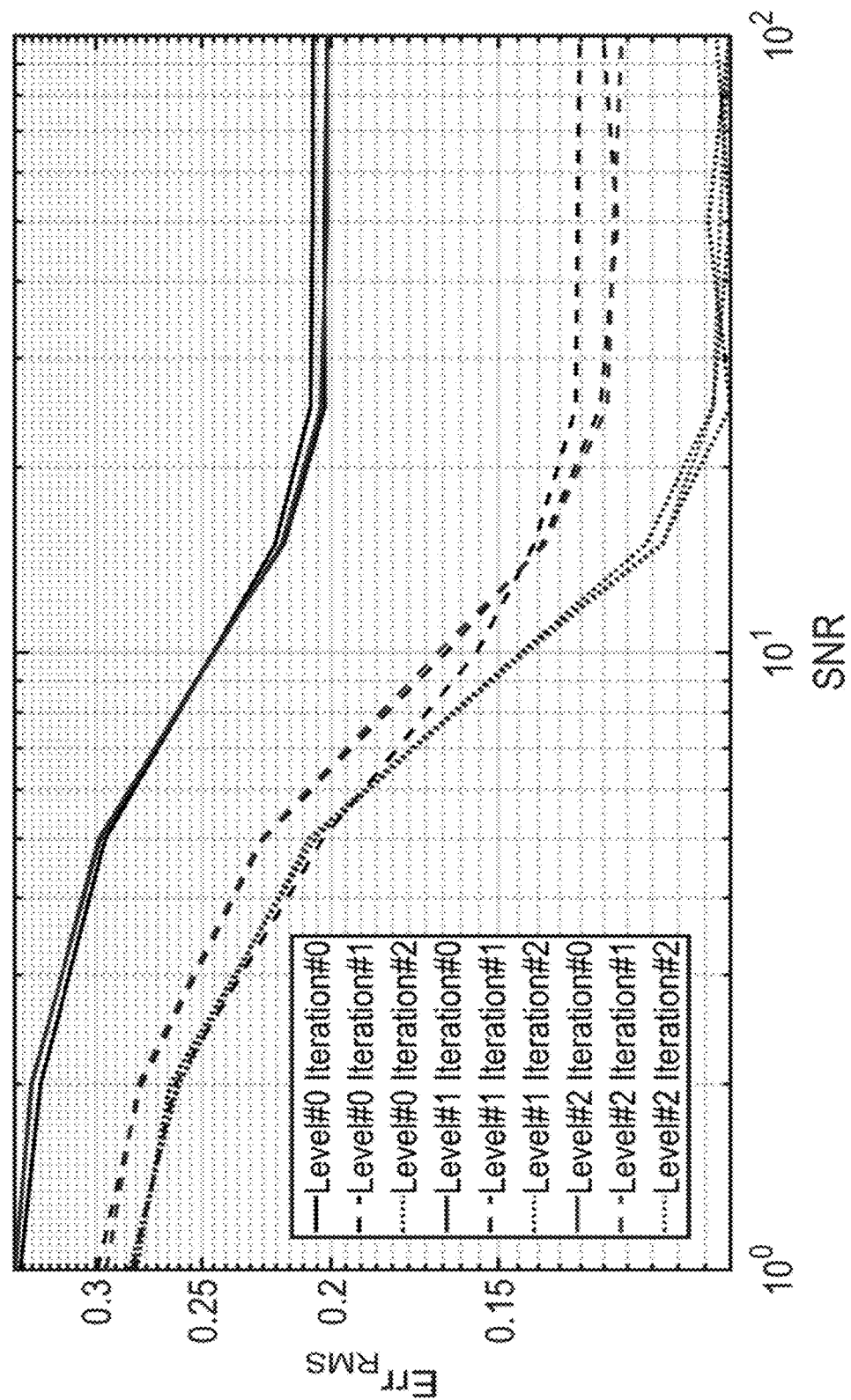
FIG. 23: The effects of hierarchical PIV, velocity correction (number of iterations), and signal to noise ratio on root mean square error (RMS).

FIG. 20 illustrates the two volumetric brightness fields that were generated according to the velocity field that defines Hill's spherical vortex. Three perpendicular slices of each frame are shown in FIG. 20. As can be seen, the corresponding slice is warped according to the given velocity V(x) and implementing pseudocodes 1 and 2. B(x) and B*(x) were then processed by V-Echo-PIV 3D velocimetry code. The velocity contours and streamlines associated with transformation of B(x) to B*(x) are illustrated in FIG. 21. FIGS. 22 and 23 show how hierarchical PIV, number of iterations for velocity correction, and signal-to-noise ratio affects RMS error. For level 0, where there were no coarsening and refining, convergency was achieved when velocity was corrected three times, with a slight difference in RMS error compared to using two-time velocity correction (two-time iterations). Accordingly, we inferred that additional iterations in our software improve the RMS error, bringing the results in better agreement with the analytical HSV. It was also observed that regardless of the number of levels, i.e., how many times the 3D dataset coarsened and refined, velocity correction significantly enhanced the results and it was found to be dependent on the value of SNR. In other words, when the signal to noise ratio in the second frame was 1, velocity correction by three times reduced the RMS error by about 18% whereas this reduction happened to be approximately 50% at SNR=100. In fact, the less noisy the data, the closer the results to the analytical HSV. For this particular flow field, considering hierarchical PIV did not found to be as effective as taking advantage of iteration and velocity correction at a fixed level of hierarchy.

At a fixed number of iterations, using different levels of coarsening and refining, affected the RMS error depending on the value of SNR. At zero number of iterations, i.e., when velocity was not corrected, incorporating coarsening/refining the dataset only improved the RMS error when SNR>10. However, for SNR<10, leveling did not enhance the RMS. When the velocity was corrected for one time, the improvement was seen when SNR was greater than 15. Using more velocity corrections, the improvement was found to happen randomly due to approaching the convergency because of using more iterations.

This study describes a framework that systematically generates a 3D brightness field using a randomly-generated field according to a known 3D velocity field. This framework provides a basis for validating 3D PIV methods. To show the efficacy of the framework, we used our in-house V-Echo-PIV software to obtain the HSV velocity field from the synthetically-generated brightness fields at a variety of SNRs. We found a close agreement between the computed velocity field and the analytical Hill's vortex.

Example 4

Figure 24:
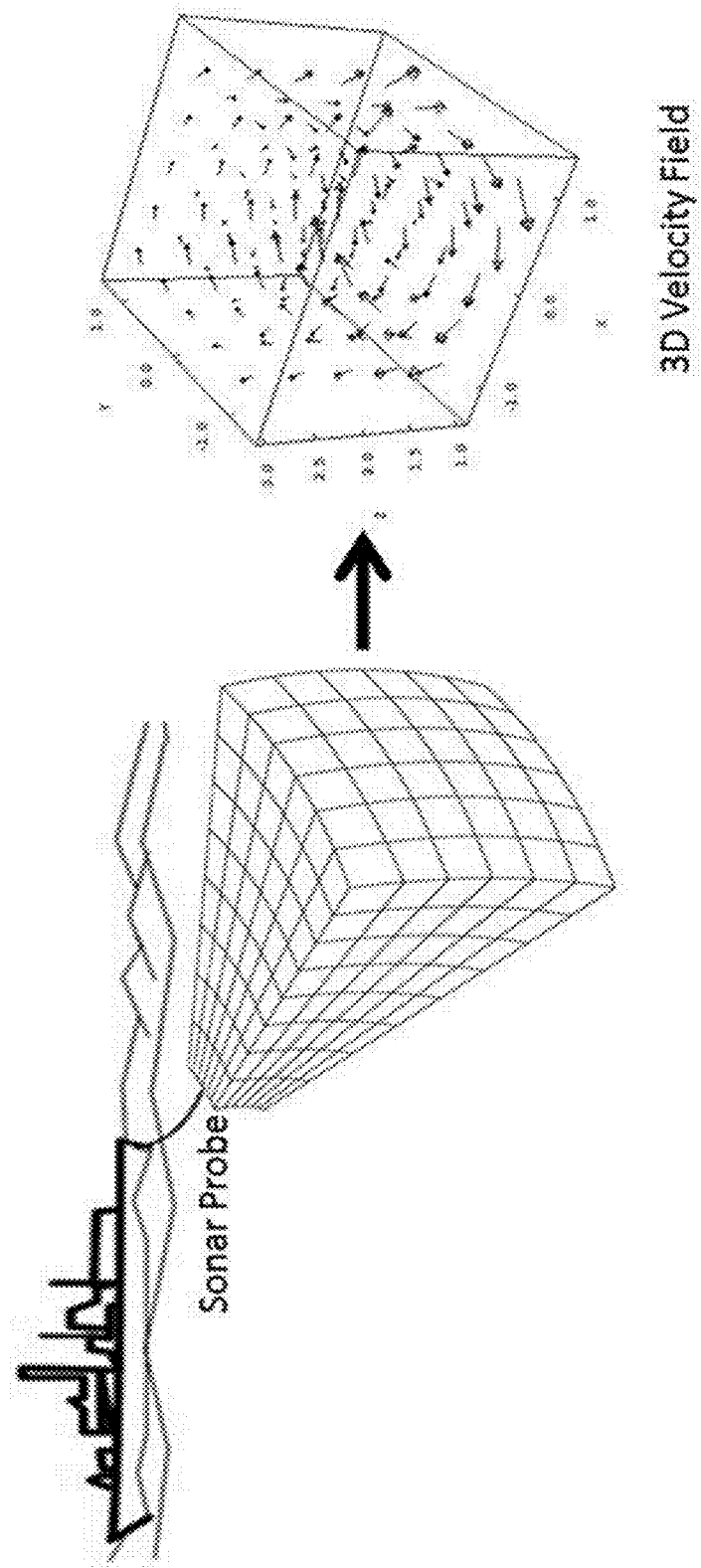
FIG. 24. Schematic of measuring an underwater flow.

Ultrasound-Based Volumetric Particle Tracking Method for Underwater Applications The measurement methods described herein are used as a measurement of underwater, three-dimensional flows, where the velocity field is obtained using ultrasound. Direction and magnitude of velocity are determined within range of a sonar probe. Such measurement methods are depicted in FIG. 24.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. A method of determining a configuration of constituents in a medium and a rate of motion of the medium, wherein the method comprises:
   using a volumetric (3D) ultrasound or sonar imaging device to capture ultrasound or sonar images or datasets of at least two volumetric frames of the medium that comprise a change over time in the configuration of the constituents in the medium, wherein the change is related to the rate of motion of the medium;
   measuring a field in the at least two volumetric frames;
   calculating a 3D velocity vector field for the at least two volumetric frames, using a processor programmed to scale velocities according to voxel size and time gap between volumetric frames,
   wherein the 3D velocity vector fields are calculated from the equation relating the configuration of the constituent in the medium to the velocity field by (1):

$$\frac{\partial B}{\partial t} + \vec{v} \cdot \vec{\nabla} B = 0, \tag{1}$$

where B is the acquired brightness scalar field in the region of interest, t is time, $\vec{v}$ is the local 3D velocity vector, and $\vec{\nabla}$ is the gradient operator;
   determining the configuration of the constituents in the medium and the rate of motion of the medium from the scaled 3D velocity vector fields; and
   displaying an image showing the configuration of the constituents in the medium and the rate of motion of the medium.

2. The method of claim 1, wherein said calculating a 3D velocity vector field for the at least two volumetric frames further comprises interpolating velocities ($v_{x1}$, $v_{x2}$, and $v_{x3}$) of the constituents in the medium for each of the at least two volumetric frames and determining the configuration of the constituents in the medium and the rate of motion of the medium from the interpolated and scaled 3D velocity vector fields.

3. The method in claim 1, wherein the configuration is an arrangement of constituents of the medium.

4. The method in claim 1, wherein the constituents are added to the medium, wherein the added constituents are not intrinsic to the medium.

5. The method in claim 1, where the medium is a compressible or an incompressible fluid.

6. The method of claim 1, wherein the field is a brightness field inherent to the medium or its motion.

7. The method of claim 6, wherein said brightness field is inherent to the medium or its motion results from medium natural components.

8. The method of claim 7, wherein said medium natural components are blood components.

9. The method of claim 1, wherein the brightness field is from a tracking agent comprising floating particles detectable in the medium during flow of the medium.

10. The method of claim 1, wherein data are stored in a multidimensional array that represents a quantity in three dimensional space and time.

11. The method of claim 10, wherein the quantity represents brightness field.

12. The method of claim 10, wherein the spatial location of the quantity is known at the time of the acquisition once the data is acquired by the volumetric (3D) ultrasound or sonar imaging device.

13. The method of claim 12, wherein the volumetric (3D) ultrasound or sonar imaging device is a sonar-based device.

14. The method of claim 12, wherein the volumetric (3D) ultrasound imaging device comprises an ultrasound transducer that measures length, width, height and time.

15. The method of claim 10, wherein the data in the multidimensional array are optimized.

16. The method of claim 10, wherein said data are optimized by a method selected from the group consisting of adjusting contrast, adjusting brightness, adjusting sharpness, noise reduction, and motion deblurring of images or datasets.

17. The method of claim 1, wherein motion of the medium or deformation of the medium is detected in open medium space.

18. The method of claim 1, wherein a solid or deformable boundary of the medium is identified and tracked.

19. The method of claim 1, wherein a change in the medium is imposed.

20. The method of claim 19, wherein an improvement in the medium is imposed.

21. The method of claim 18, wherein the solid or deformable boundary of the medium corresponds to a wall enclosing the medium.

22. The method of claim 18, wherein the solid or deformable boundary of the medium is tracked by a method selected from the group consisting of a manual method, a semi-automatic method, and an automatic method.

23. The method of claim 22, wherein said automatic method is selected from the group consisting of multi-planar segmentation, active contour tracking, speckle tracking, machine learning, and artificial intelligence method.

24. The method of claim 19, wherein said change in the medium configuration comprises imposing one or more governing equations of physics to the results.

25. The method of claim 1, wherein said medium is a body of water and the method measures an underwater, three-dimensional flow.

26. The method of claim 25, wherein direction and magnitude of flow velocity are determined within range of a sonar or radar probe.

27. The method of claim 1, further comprising displaying an image showing the solid or deformable boundary of the medium.

28. The method of claim 1, where the 3D velocity vector fields are visualized.

29. The method of claim 28, where the visualization is done by at least one streamline, pathline, streakline, or particles.

30. The method of claim 1, where fluid dynamics-related quantities are derived from the 3D velocity vector fields.

31. The method of claim 1, where the 3D velocity vector fields, their properties, or velocity dependent quantities are used for diagnosis, detection of at least one disorder, decision making, or therapeutic purposes.

32. The method of claim 1, where the functionality of the medium is assessed based on the 3D velocity vector fields.

33. The method of claim 32, where the functionality is expressed in terms of vorticity, kinetic energy, energy dissipation, shear stress, pressure, vortex formation time, or particle residence time.

34. The method of claim 32, where the functionality of the deformable body is assessed using the 3D velocity vector fields.

35. The method of claim 1, where vortices are imaged using the velocity field.

36. The method of claim 30, where the fluid dynamic quantity is pressure or pressure difference.

37. The method of claim 1, where equation (1) is solved locally.

38. The method of claim 1, where equation (1) is solved globally for an entire configuration field.

39. The method of claim 1, where equation (1) is solved by combining local and global methods.

40. The method of claim 1, where a configuration of the field is coarsened at least one time.

41. The method of claim 40, where the 3D velocity vector fields are solved in at least one coarsened configuration.

42. The method of claim 41, where the 3D velocity vector fields are interpolated from at least one coarsened configuration to at least one refined configuration.

43. The method of claim 42, where at least one correction velocity field is obtained.

44. The method of claim 43, where the correction velocity field is applied to a refined configuration.

45. The method of claim 40, where the process of coarsening configurations is repeated.

46. The method of claim 42, where the process of interpolating to a finer configuration is repeated.

47. The method of claim 43, where the process of obtaining the correction velocity field is repeated.

48. The method of claim 44, where the process of applying the correction to the refined configuration is repeated.

49. The method of claim 24, where at least one correction field is obtained by using at least one physical constraint.

50. The method of claim 1, where equation (1) is expressed in a Cartesian coordinate system:

$$\frac{\partial B}{\partial t} + v_x \frac{\partial B}{\partial x} + v_y \frac{\partial B}{\partial y} + v_z \frac{\partial B}{\partial z} = 0.$$

51. The method of claim 1, where equation (1) is expressed in a spherical coordinate system:

$$\frac{\partial B}{\partial t} + v_r \frac{\partial B}{\partial r} + v_\theta \frac{1}{r} \frac{\partial B}{\partial \theta} + v_\varphi \frac{1}{r \sin\theta} \frac{\partial B}{\partial \varphi} = 0.$$

52. The method of claim 24, where the physical governing equation is the incompressibility of the medium.

* * * * *